US012663422B2

(12) United States Patent
Ahmad

(10) Patent No.: US 12,663,422 B2
(45) Date of Patent: Jun. 23, 2026

(54) METHOD FOR DETECTION OF CD16b

(71) Applicant: 52 NORTH HEALTH LTD, Cambridge (GB)

(72) Inventor: Saif Ahmad, Cambridge (GB)

(73) Assignee: 52 North Health Ltd, Cambridge (GB)

( * ) Notice: Subject to any disclaimer, the term of this patent is extended or adjusted under 35 U.S.C. 154(b) by 809 days.

(21) Appl. No.: 17/916,415

(22) PCT Filed: Apr. 1, 2021

(86) PCT No.: PCT/GB2021/050813
§ 371 (c)(1),
(2) Date: Sep. 30, 2022

(87) PCT Pub. No.: WO2021/198693
PCT Pub. Date: Oct. 7, 2021

(65) Prior Publication Data
US 2023/0138656 A1 May 4, 2023

(30) Foreign Application Priority Data

Apr. 3, 2020 (GB) ...................................... 2004972

(51) Int. Cl.
*G01N 33/569* (2006.01)
*G01N 33/543* (2006.01)
(52) U.S. Cl.
CPC . *G01N 33/56972* (2013.01); *G01N 33/54388* (2021.08); *G01N 2333/70535* (2013.01)
(58) Field of Classification Search
CPC ....... G01N 33/54386; G01N 33/54387; G01N 33/54388; G01N 33/558; G01N 33/56972
See application file for complete search history.

(56) References Cited

U.S. PATENT DOCUMENTS

| 2004/0048274 A1* | 3/2004 | Breindahl | G01N 33/543 |
| | | | 435/7.9 |
| 2013/0130286 A1* | 5/2013 | Silverstein | G01N 33/6893 |
| | | | 435/7.92 |
| 2014/0273018 A1* | 9/2014 | Bystryak | G01N 33/5047 |
| | | | 435/287.2 |
| 2019/0170749 A1* | 6/2019 | Anderson | G01N 33/56972 |

FOREIGN PATENT DOCUMENTS

| WO | 2002033408 | 4/2002 |
| WO | 2018018095 | 2/2018 |

OTHER PUBLICATIONS

Office Action dated Feb. 1, 2024 for Canadian Application No. 3,173,438, 7 pp.
Riera et al. (2010) "Anti-polymorphonuclear neutrophil antibodies in patients with leukopenia or neutropenia" Int. Jnl. Lab. Hem., 32:e96-e105.

* cited by examiner

*Primary Examiner* — Gailene Gabel
(74) *Attorney, Agent, or Firm* — Brian E. Davy; Bozicevic, Field & Francis LLP

(57) ABSTRACT

The invention provides methods of determining the neutrophil level in a sample by determining the level of CD16b, including the intracellular form of CD16b in a sample, such as a blood sample. The methods may further comprise the determination of lactate levels Also provided are associated diagnostic and therapeutic methods. Further provided are kits and devices for performing the methods, particularly lateral flow kits and devices.

17 Claims, 13 Drawing Sheets

Cell-associated CD16b against neutrophil levels $R^2 = 0.5349$

Cell-associated CD16b against neutrophil levels $R^2 = 0.5349$

METHOD FOR DETECTION OF CD16b

FIELD OF THE INVENTION

The present invention relates to detecting CD16b and the use thereof in determining neutrophil levels, particularly via a lateral flow assay. In particular, the invention provides methods for determining the neutrophil level in a sample and the use of such methods for diagnosing neutropenia and/or sepsis. Various other aspects of the invention provide devices and kits for carrying out such methods.

BACKGROUND TO THE INVENTION

Neutrophils are the most abundant white blood cell in humans and mice. They are 12-1 μm in diameter and have a half-life in the peripheral blood circulation of 6-8 hours. Neutrophils make up 40-80% of the total white blood cell count and their normal range is around 1500 to 7500 cells/μL. Neutrophils represent the first line of defence in response to invading microbes, by phagocytosis of pathogens and/or release of antimicrobial factors contained in specialised granules.

Chemotherapy is an example of a treatment that reduces the production of white blood cells, including neutrophils by the bone marrow, resulting in a drop in circulating neutrophil cell numbers. When neutrophil levels drop to below 1500 cells/μL blood, the subject has neutropenia. As neutrophils act as the first line of defence against infection, dramatically reduced levels leave patients susceptible to microbial attack. Neutropenia at levels below 1000 cells/μL is deemed to be particularly clinically relevant in terms of reducing a patient's ability to fight infections. As such, neutropenia puts patients at risk of neutropenic sepsis.

Neutropenic sepsis (NS) is a potentially life-threatening complication of, for example, cancer chemotherapy and immunosuppressive treatments. It is defined by symptoms of sepsis (including a temperature above 38° C.) along with a neutrophil count of $0.5 \times 10^9$/L or lower (National Institute for Health and Care Excellence (NICE) 2012). It is a relatively common condition, causing the death of about 1 in 500 patients diagnosed with cancer.

Clinical guidelines recommend that patients at risk of NS (e.g. those on chemotherapy) with even mild signs of infection (e.g. mild fever), immediately attend hospital and receive life-saving intravenous antibiotics on an urgent basis (e.g. within one hourly. These patients have a blood test (including neutrophil levels), and whilst awaiting the results (up to 2 hours), are automatically given antibiotics in case they have NS.

Significantly, around 50% of patients have normal neutrophil levels and therefore did not necessarily need to attend hospital or receive antibiotics. Many of these patients have mild viral infections and could have been reviewed by their general practitioner, if the risk of NS had been ruled out. These unnecessary admissions are costing the NHS around £40 million per year.

Sepsis is a potentially life-threatening condition caused by the body's response to an infection. Whilst NS is associated with low neutrophil counts, in non-neutropenic subjects (i.e. most of the general population) sepsis is frequently associated with increased neutrophil counts of over 7500 cells/μL blood. Sepsis is a leading cause of death in the United Kingdom, with a mortality of 25-30% for severe cases.

Neutrophil counts can be determined using, for example, flow cytometry, which requires the use of a flow cytometer.

DESCRIPTION OF THE INVENTION

The present inventors provide methods for detecting CD16b as a neutrophil cell marker.

CD16 (a cluster of differentiation molecule found on the surface of certain white blood cells) is an IgG cell surface receptor. It is a type III Fcγ receptor (fragment, crystallisable). In humans it exists in two relatively homologous forms—CD16a and CD16b (also known as FcγRIIIa and FcγRIIIb respectively). CD16a is a transmembrane protein, whereas CD16b is anchored by a glycosyl-phosphatidylinositol (GPI) linker to the plasma membrane (Zhang et al., 2000).

CD16 proteins are expressed on the surface of neutrophils in over 99% of the population. CD16 functions in phagocytosis, degranulation, and oxidative burst. CD16b also specifically functions in removal of soluble immune complexes from blood vasculature. CD16a is expressed by neutrophils, T cells, monocyte/macrophages, NK cells, mast cells and dendritic cells. They are most abundantly found on neutrophils (i.e. only 20% of monocytes express CD16). CD16b is expressed on neutrophils and to a far lesser extent on basophils and activated eosinophils, which comprise only 1-5% of all white blood cells.

Each neutrophil cell is estimated typically to express between 100,000 and 200,000 copies of CD16b. CD16b together with FcγRIIa (CD32a) activates phagocytosis, neutrophil degranulation, and oxidative burst, to tackle pathogens (Jianga et al 2016). CD16b is shed from neutrophils via protease action during activation and apoptosis, resulting in a soluble fraction in blood. However, it is also rapidly replenished to the cell surface by intracellular stores. CD16b shedding involves cleavage of the stalk region of Cd16b by a protease, believed to be ADAM17. The cleavage site is believed to be between Ala195 and Val196.

The inventors have determined that there is a good positive correlation between the levels of CD16b and neutrophil counts. In particular, as shown in the Examples, the inventors have isolated white blood cells, including neutrophils, from blood samples and split the resulting cell solutions into 2 halves. Neutrophil counts of one half were determined using flow cytometry. The white blood cells (including neutrophils) present in the other half were lysed and CD16b levels were determined. A good positive correlation between neutrophil counts and CD16b levels was determined.

Specifically, the inventors have determined that there is a good positive correlation between the levels of intracellular and membrane-anchored CD16b (i.e. cell-associated CD16b) and neutrophil counts. Importantly, the correlation between intracellular and membrane-anchored CD16b and neutrophil counts is much better than the correlation between the soluble CD16b and neutrophil counts. Accordingly, it is a preferred embodiment of all of the aspects of the invention that the detected CD16b or determined CD16b level includes the intracellular form of CD16b and more preferably also the membrane-anchored form of CD16b and even more preferably excludes at least a proportion of the soluble form of CD16b that was present in the subject's sample. Thus, any reference herein to the 'detection of CD16b' or 'detected CD16b', or to the 'determination of the levels of CD16b' or 'CD16b levels' should be understood to include as a preferred embodiment that the CD16b includes the intracellular form of CD16b and more preferably also the membrane-anchored form of CD16b and even more prefer-ably excludes at least a proportion of the soluble form of CD16b that was present in the subject's sample.

Accordingly, in one aspect, the invention provides the use of CD16b as a marker for neutrophils in a sample. Any discussion herein to a "marker" should therefore be under-stood to encompass the embodiment that the marker is CD16b, unless specified otherwise.

The inventors have developed a lateral flow assay for the detection of CD16b. The assay may be used to determine the level of CD16b in a sample.

Thus, provided is a method of detecting CD16b in a sample, the method comprising detecting CD16b, and/or determining the level of CD16b, using a lateral flow assay. Preferably, any of the methods or uses provided herein employ a lateral flow assay for the detection of CD16b and/or the determination of the level of CD16b.

Also provided is a method of detecting neutrophils and/or determining the neutrophil level in a sample, the method comprising detecting CD16b, and/or determining the level of CD16b. The presence and/or level of neutrophils may be determined on the basis of the presence or level of the detected CD16b. Preferably, the (detected) CD16b com-prises the intracellular form of CD16b. More preferably still, the (detected) CD16b comprises, consists essentially of, or consists of the membrane-anchored form of CD16b and the intracellular form of CD16b.

Blood lactate in circulation can be used as a marker for systemic tissue hypoperfusion and cellular dysfunction in sepsis patients. Thus, the method may further comprise a step of detecting lactate in a sample. The method may further comprise detecting one or more different markers indicative of the presence of (neutropenic or non-neutropenic) sepsis in the sample. The method may further comprise a step of detecting lactate, and/or determining the level of lactate, in the sample. The step of detecting lactate, and/or determining the level of lactate may be carried out (i) before determining the level of CD16b, (ii) before any step of cell lysis, (iii) on a solution comprising soluble components of the sample, and/or (iv) via a lateral flow assay.

The method of detecting neutrophils and/or determining the neutrophil level in a sample may comprise:

(a) a step of filtering the sample to yield:
  (i) a filtered sample comprising white blood cells, wherein the white blood cells comprise neutrophils, wherein the filtered sample is preferably depleted of the soluble components of the sample, particularly the soluble form of CD16b; and
  (ii) a solution comprising soluble components of the sample; wherein the solution is preferably white blood cell-free or at least neutrophil-free, but may comprise red blood cells;
(b) a step of cell lysis of the filtered sample from (i);
(c) a step of determining the level of CD16b in the sample from (b), optionally on a first lateral flow strip; and optionally
(d) a step of detecting lactate or determining the lactate level in the solution of (ii), optionally on a second lateral flow strip,
  wherein step (d), if present, may be simultaneous or sequential with step (b) or (c).

Preferably, lactate is detected and/or the level of lactate is determined using lactate dehydrogenase and a reagent, pref-erably wherein the reagent is a coloured reagent, more preferably wherein the reagent changes the colour upon the action of lactate dehydrogenase in the presence of lactate.

The method may comprise the steps of:
i. adding a sample to a first sample application zone of a first test strip to trap any neutrophils on a filter com-prised within the first test strip;
ii. transferring the filter with trapped neutrophils to a second sample application zone of a second test strip;
iii. adding to the filter a lysis reagent to lyse the neutro-phils; and
iv. determining the level of CD16b.

Preferably, the step of determining the level of CD16b comprises:
i. contacting the lysed neutrophils with a conjugate zone comprising at least one labelled detection moiety which binds to CD16b;
ii. contacting the mixture of the lysed neutrophils and the at least one labelled detection moiety which binds to CD16b with:
  (i) a test line for at least CD16b, the test line comprising an immobilised further detection moiety that also binds to CD16b thereby immobilising the CD16b at the test line to produce a signal via the labelled detection moiety also bound to the CD16b; or
  (ii) a test line for at least CD16b, the test line com-prising an immobilised further detection moiety that binds to the CD16b-bound labelled detection moiety of step ii. thereby immobilising it at the test line producing a signal.

The lysis reagent may be a surfactant, which may be ionic or non-ionic, such as Triton X-100. The lysis reagent should be a membrane-solubilizing reagent.

The labelled detection moiety which binds to CD16b may be an anti-CD16b antibody conjugated to a detectable label, such as a gold particle. The further detection moiety may be an anti-CD16b antibody, preferably a polyclonal antibody. The step of adding the sample to the first application zone may be followed by a step of cell wash. The filter may be a membrane suitable for trapping neutrophils. In one embodi-ment, transferring the membrane with trapped neutrophils is done manually or automatically. The method may further comprise detecting lactate, and/or determining the level of lactate, in the sample.

Also provided is a device, system, kit, or testing compo-sitions of matter, suitable for, or specifically adapted for, performing one or more of the methods provided herein. The invention may be performed using systems, devices, testing kits or testing compositions of matter as described herein.

Unless otherwise stated, by "CD16b" is meant the CD16b protein. The CD16b may comprise, consist essentially of, or consist of the membrane-anchored form of CD16b (more particularly the glycosylphosphatidylinisotol (GPI) anchored form of CD16b) and/or the intracellular form of CD16b. To facilitate the detection of the intracellular form of CD16b, the method may comprise a step of cell lysis, or be carried out on a sample that was pre-treated to achieve cell lysis. The step of cell lysis should lyse at least a proportion of the neutrophils present in the sample. Prefer-ably, the cell lysis step results in lysis of at least 50, 60, 70, 80, 90, 95, 96, 97, 98, or 99%, or substantially all of the neutrophils. The cell lysis may be full or partial. Preferably, the cell lysis at least partially, preferably substantially, solubilises the neutrophil cell membrane. Preferably, the cell lysis at least partially, preferably substantially, solubilises the neutrophil intracellular membranes. Thus, the term "cell lysis" is used herein to denote that the cell membrane is at least partially disrupted; bursting of the cell is not neces-sarily required. The cell lysis may release the intracellular form of CD16b, or otherwise make it accessible to the detection moiety, such as an anti-CD16b antibody. Cell lysis may, for example, be achieved through the use of a suitable surfactant, which may be ionic or non-ionic, for example Triton x100.

The step of cell lysis may preferably be performed for at least 10, 20, 30, 40, or 50 seconds and/or no more than 30, 20 or 10 minutes; about 1-5 minutes or about 3-5 minutes is preferred.

The step of cell lysis may be carried out:
(i) after a step of removing at least a proportion of the soluble CD16b; or
(ii) on a sample from which at least a proportion of the soluble CD16b has previously been removed.

The method may further comprise a step of removing at least a proportion, and preferably most or all, of the soluble form of CD16b from the sample prior to determining the level of CD16b. The method may be performed on a sample from which at least a proportion, and preferably most or all, of the soluble form of CD16b has previously been removed. The step of removing at least a proportion of the soluble form of CD16b may be a filtration and/or wash step, wherein the filtration and/or wash step preferably yields:
(i) a filtered and/or washed sample comprising white blood cells, preferably neutrophils, wherein the filtered and/or washed sample is preferably depleted of the soluble components of the sample; and
(ii) a solution comprising soluble components of the sample; wherein the solution is preferably white blood cell-free, preferably neutrophil-free, but may comprise red blood cells.

The step of removing at least a proportion of the soluble form of CD16b from the sample may be carried out under conditions that keep at least a large proportion, and preferably substantially all, of the neutrophils present in the sample intact and preferably alive (non-apoptotic).

By "GPI anchored form of CD16b", which is herein used interchangeably with "membrane-anchored form of CD16b" or "membrane-anchored CD16b" is meant CD16b that is anchored to the cell membrane in an intact neutrophil. This term should be understood to encompass CD16b that was anchored to the cell membrane in an intact neutrophil prior to subjecting the neutrophil to a step of cell lysis. Thus, as a result of cell lysis, the GPI anchored form of CD16b may be anchored to a cell membrane fraction, or released from the cell membrane, but should nevertheless be considered to be the "GPI anchored form of CD16b".

By the "intracellular form of CD16b" is meant CD16b that is present inside of the cell in an intact neutrophil. Neutrophils typically contain intracellular pools of CD16b, which can be translocated to the membrane, for example to replace membrane-anchored CD16b that was shed from the membrane (i.e. soluble CD16b). Thus, the term "intracellular form of CD16b" encompasses such CD16b pools.

This term should be understood to encompass CD16b that was intracellular in an intact neutrophil prior to subjecting the neutrophil to a step of cell lysis. Thus, as a result of cell lysis, the intracellular form of CD16b may be released from the cell, but should nevertheless be considered to be the "intracellular form of CD16b".

Chemoattractants may stimulate the translocation of CD16b from intracellular pools to the surface of neutrophils. Thus, CD16b may transition from "intracellular CD16b" to "GPI anchored CD16b".

Both the "GPI anchored form of CD16b" and the "intracellular form of CD16b" may be considered to be a form of CD16b that was not actively shed by a neutrophil, or was not actively shed prior to the sample being taken from the subject. In other words, both the "GPI anchored form of CD16b" and the "intracellular form of CD16b" typically have not been cleaved by a protease such as ADAM17 and therefore typically have an intact stalk region. They may also be referred to as "intact" or "non-truncated" or "non-soluble" CD16b.

In preferred embodiments of any of the aspects provided herein, the CD16b comprises, consists essentially or consists of a combination of the "GPI anchored form of CD16b" and the "intracellular form of CD16b". Thus, it preferably comprises, consists essentially or consists of "intact" CD16b.

In some embodiments, the CD16b comprises the soluble form of CD16b. In other embodiments, the CD16b does not comprise the soluble form of CD16b. Thus, the method may comprise a step of removing the soluble form of CD16b from the sample, or be carried out on a sample that was pre-treated to remove the soluble form of CD16b.

By the "soluble form of CD16b" is meant CD16b that has been actively shed by neutrophils. As mentioned above, shedding involved cleavage in the stalk region, so the soluble form typically lacks the C-terminal amino acids, e.g. lacks the C-terminal region up to Val196 or Ala195. The soluble form may therefore be referred to as "truncated", particularly "C-terminally truncated".

By "removing" is meant in this context that at least a proportion of the soluble form of CD16b is removed, e.g. at least 20, 30, 40 or 50%, preferably at least 60, 70, 80, 85, 90, 95 or 99%.

Neutrophils may continuously shed at least some CD16b, so it will be understood that a complete removal of all the soluble form of CD16b from a sample may not be possible, because any neutrophil-containing sample will typically contain some freshly shed CD16b. Sample handling conditions such as temperature and pH may influence the level of shedding and the method may comprise a step using or adjusting such conditions to minimise shedding.

Preferably, at least a substantial proportion of the soluble form of CD16b is removed. Alternatively viewed, the removal increases the ratio of neutrophils to the soluble form of CD16b, for example increases it 2, 3, 4 or 5 or 10 fold. Alternatively viewed, the removal ensures that the level of any the soluble form of CD16b detected by the assay does not impact on the determination of the neutrophil level. For example, after removal, the level of any the soluble form of CD16b may be insignificant, or, due to any fresh shedding, show a positive correlation with neutrophil levels.

Such removal may, for example, involve a step of forming a cell pellet, for example by centrifugation, and removing at least some of the fluid, such as the supernatant. One or more wash steps may be employed.

Alternatively, such removal may involve a step of filtering the sample to separate soluble CD16b from neutrophils. It will be understood that such a step would be carried out before the remaining step(s) is/are carried out to detect CD16b, for example before any cell lysis step, if used.

For example, the sample containing white blood cells (e.g. neutrophils) may be deposited on a filter, for example a suitable membrane which acts as a filter, wherein white blood cells (e.g. neutrophils) from the sample get trapped in or on the filter.

The filter should be suitable for, e.g. configured to (i) trap cells including neutrophils; or (ii) specifically trap neutrophils. The filter may thus "trap" neutrophils. By "tapping" neutrophils is meant that neutrophils are retained on the surface and/or within the filter, whereas other components of the sample, particularly components such as soluble CD16b and preferably also red blood cells are not trapped by the filter. It will be understood that the filter may not trap 100% of the neutrophils present in the sample, but it should trap the majority or a significant proportion of the neutrophils, preferably at least or about 70, 80, 85, 90, 92, 94, 95, 96, 97, 98 or 99% of the neutrophils present in the sample.

In some embodiments, other cell types present in the sample may also be trapped by the filter, but in other embodiments, other cells types are not trapped. Preferably, red blood cells are not trapped by the filter. Thus, preferably the filter is configured selectively to trap white blood cells, particularly neutrophils.

Thus, the sample may be filtered using a suitable filter that allows the separation of neutrophils from soluble CD16b, for example by size exclusion and/or adsorption. The filter may include a suitable matrix, such as Leukosorb™, for example as part of the Acrodisc® White Blood Cell Syringe Filter, both available from Pall Life Sciences, 600 South Wagner Road Ann Arbor, MI 48103-9019, USA. The filter may preferably be or comprise a membrane, such as a microporous membrane. Blood separation membranes are known. A filter suitable for use in the kits, devices and methods of the present invention includes any filter suitable for trapping neutrophils, for example, FR1 or FR2 blood separator pad (available from Mdi Membrane Technologies, 20-21 Industrial Area, Ambala Cantt 133 006, INDIA)), such as FR1 R2990/998/1). The filter may be an integral part of the detection device; be a modular part of the detection device; or be separate from the detection device. For example, the filter and the detection device may be provided as part of a kit. As mentioned elsewhere herein, the detection device is preferably a lateral flow device. For example, the filter may act as a sample application pad and/or be in a sample application zone.

In some embodiments, the sample may contain sufficient fluid to allow neutrophils to become trapped by the filter whilst allowing other sample components, particularly soluble CD16b and preferably also red blood cells, to pass through the filter. However, in preferred embodiments, after the sample has been applied to the filter, a suitable fluid is applied to the filter to remove sample components other than white blood cells, particularly soluble CD16b and preferably also red blood cells. For example, non-white-blood-cell components may be flushed off the filter. The solution may, for example, be a buffer. Such a step of removing sample components other than white blood cells may be referred to as a 'wash' step. Thus, the filtration step may preferably include a wash step and any reference to 'filtration' should be understood to encompass the preferred embodiment of filtration including a wash step, unless otherwise stated.

The fluid is preferably a buffer and should be selected to ensure that the neutrophils remain intact and preferably viable (non-apoptotic).

Preferably, during the filtration step at least 50%, 60%, 70, 80%, 90% or 100% of the non-white blood cell (e.g. non-neutrophil) components of the sample are removed with a solution. Preferably, all non-white blood cell (e.g. non-neutrophil) components of the sample are removed from the filter.

The filtration step may yield a solution comprising soluble components of the sample; wherein the solution is preferably white blood cell-free or at least neutrophil-free but may comprise red blood cells. This solution may be assayed, for example to determine the level of lactate.

After the filtration step, the method may involve a step of bringing the filter into fluid communication with a vessel or the/a sample pad or sample application zone of the lateral flow device. For example, this may include transferring the filter with trapped white blood cells (e.g. neutrophils) from a first sample application zone to a second sample application zone. The transfer may be done manually or automatically. This may involve contacting the filter and vessel or sample pad or sample application zone; or using a fluid to flush the white blood cells (e.g. neutrophils) from the filter into the vessel or into the sample pad or sample application zone. It may involve rotating the filter, for example by about 90 or about 180 degrees around the origin; or turning the filter over (such that the surface that was facing upwards is positioned to face downwards); or otherwise positioning and angling the filter in an appropriate manner. The manual or automatic transfer may be done with use of forceps or by flipping the filter from a first position, such as initial first assay zone or compartment, to a second position, such as the zone or compartment of CD16b detection.

For example, during the filtration step, a sample comprising neutrophils may be added to a filter, e.g. a membrane in a first sample application zone of a first test strip. The filter with trapped neutrophils may be transferred to a second sample application zone of a second test strip. Preferably, the filter traps neutrophils and is washed prior to transfer to the second sample application zone.

For example, the sample may be filtered to capture the white blood cells. Optionally, the filtrate may be collected separately. The white blood cells (e.g. neutrophils) may subsequently be lysed whilst in contact with the filter, for example using a lysis buffer (e.g. containing a surfactant). Alternatively, the cells may be eluted from the filter, for example into a vessel or onto a device or test strip.

The filtration step, if used, should be performed under conditions that keep neutrophils intact and preferably non-apoptotic (i.e. neutrophils are kept live). Thus, white blood cells (e.g. neutrophils) should be trapped in or on the filter in a manner and under conditions that minimise white blood cell (e.g. neutrophil) apoptosis and lysis. Preferably, less than 50%, 40%, 30%, 20%, 10%, or 5% of white blood cells (e.g. neutrophils) are lysed or undergo apoptosis during the filtration step. Preferably, more than 50%, 60%, 70, 80, 90%, 95% of white blood cells (e.g. neutrophils) have not been lysed or undergone apoptosis during the filtration step. If a filtration step is used, white blood cell (e.g. neutrophil) lysis should (substantially) only take place after the filtration step.

After such a filtration step (if used), the white blood cells (e.g. neutrophils) may be contacted with a cell lysis reagent, such as a surfactant, prior to, concomitantly with or after contacting the white blood cells with a test device or test strip. Thus, the test device may comprise a cell lysis reagent.

If cells, preferably white blood cells (e.g. neutrophils), are eluted (intact) from the filter, a volume of this cell suspension may, for example, be contacted with a lysis buffer and the lysed sample may then be applied to a test device or test strip. Alternatively, (intact) cells, preferably white blood cells (e.g. neutrophils), may be applied directly to a test device containing cell lysis reagent. For example, the sample pad of a lateral flow device may be impregnated with a cell lysis reagent.

In some embodiments, removal of the soluble form of CD16b may involve the use of a binding reagent, such as an antibody, that is highly selective for the soluble form of CD16b, for example that specifically recognises the C-terminal region of the soluble form of CD16b that is generated through protease cleavage during the shedding process.

In some embodiments, as an alternative or in addition to removal of the soluble form of CD16b, a reference is used to correct for the presence of the soluble form of CD16b, thereby allowing a determination of the level of the membrane-anchored form of CD16b (more particularly glyco-sylphosphatidylinisotol (GPI) anchored CD16b) and/or the intracellular form of CD16b.

The inventors have determined that the CD16b level is indicative of the neutrophil level in the sample. In turn, neutrophil levels below a certain threshold (discussed elsewhere herein) are indicative of neutropenia. Subjects with neutropenia are at an increased risk of neutropenic sepsis. Accordingly, the CD16b level is indicative of neutropenia and may be used to determine the risk of neutropenic sepsis or to diagnose neutropenic sepsis, particularly if the subject has one or more symptoms of infection, such as a temperature of above 38° C.

In any of the methods or devices provided herein, the sample may preferably be taken form the subject no more than 24 hours prior to determining the level of CD16b and optionally one or more further markers, such as lactate, preferably no more than 4, 3, 2 or 1 hours or 30, 25, 20, 15, 10 or 5 minutes prior to determining the level of CD16b and optionally one or more further markers, such as lactate.

The method of the present invention is very fast, the levels of CD16b (and optionally other markers, such as lactate) and the corresponding neutrophil levels can be determined in less than 60, 45, 30, or 15 minutes. Preferably, the levels of CD16b (and optionally other markers, such as lactate) can be determined in less than 15 min.

The method of the present invention preferably does not require a step of incubating the sample, for example with exogenously added any cell-signalling molecules, prior to performing the method steps disclosed herein.

Neutrophil levels above a certain threshold (discussed elsewhere herein) are indicative of sepsis. To distinguish such sepsis from neutropenic sepsis, the term "non-neutropenic" sepsis may be used.

Also provided is a method for predicting, diagnosing, excluding and/or monitoring neutropenia and/or neutropenic sepsis, or (non-neutropenic) sepsis, in a subject, the method comprising detecting CD16b, and/or determining the level of CD16b, in a sample. Preferably, the CD16b comprises the intracellular form of CD16b and preferably also the GPI-anchored form of CD16b and preferably excludes at least a proportion of the soluble form of CD16b.

In any of the methods provided herein, a determination of the neutrophil level in the sample may be made on the basis of the determined CD16b level (which, as discussed elsewhere herein preferably comprises the intracellular form of CD16b and preferably also the GPI-anchored form of CD16b and preferably excludes at least a proportion of the soluble form of CD16b. Although a determination of the neutrophil level may be made in this way, the CD16b level may, alternatively, conveniently be used as an indirect maker of neutropenia and/or neutropenic sepsis, or (non-neutropenic) sepsis.

The determination of the CD16b level and/or neutrophil level may, for example, be semi-quantitative or quantitative. The normal range of neutrophils in a human blood sample is around 1500 to 7500 cells/μL. Serial dilutions of samples with known neutrophil counts may be used to determine how to translate determined CD16b levels into neutrophil counts.

The CD16b level and/or neutrophil level may be determined to be above or below a predetermined threshold. Threshold levels may be defined from population studies or be specific to the individual. Where specific to the individual, the levels may reflect those taken at one or more earlier time points. Details of suitable thresholds are discussed below. It should naturally be understood that the "marker" in these passages may be CD16b, but the discussion is also applicable to any other suitable marker.

In some embodiments, the threshold level of the marker, such as CD16b, is set by determining the levels of the marker in blood samples taken from the subject at one or more earlier time points. In its simplest form, the invention may rely upon a simple comparison between the test sample and the level of the marker in the previously taken sample (i.e. a single earlier time point). However, typically, the earlier time points may comprise at least two, and possibly at least 3, 4, 5, 6, 7, 8, 9, or 10 earlier measurements preceding the determination of the level of the marker in the current sample. Those earlier measurements may be taken over a period of days or weeks, such as 1, 2, 3, 4, 5 or 6 weeks or longer. The baseline may be set during a period of healthy (non-neutropenic and non-septic) status to determine the initial thresholds against which future changes in levels are measured. Healthy (non-neutropenic and non-septic) status may initially be identified by routine methods, such as neutrophil counts via flow cytometry.

Where marker levels are measured at multiple time points those levels may be averaged to provide the threshold for the test sample. In some embodiments, the threshold may be set with reference to a sliding window within which levels of the markers have been measured to provide a baseline. The threshold level is thus "learned" by the system.

Threshold levels may be set with reference to a training data set comprising samples defined in relation to neutropenia and/or neutropenic sepsis or (non-neutropenic) sepsis status. The threshold levels may vary according to the measuring technique adopted. Example population thresholds are set forth herein.

A semi-quantitative determination may involve a determination whether or not the neutrophil level is "normal". A "normal" neutrophil level, which may also be referred to as a "healthy", "non-neutropenic" and/or "non-infected" neutrophil level, may be defined as between about 1500 to 7500 neutrophil cells/μL of blood. A "normal" CD16b, which may also be referred to as a "healthy", "non-neutropenic" and/or "non-infected" CD16b level, may be defined as the level typically found in a sample comprising between about 1500 to 7500 neutrophil cells/μL of blood. This may, for example, be equated to about 5-25 ng/ml CD16b which may, for example correspond to a cube unit reading of 25-80 CU.

A "normal" lactate level, which may also be referred to as a "healthy", "non-neutropenic" and/or "non-infected" lactate level, may be defined as the level typically found in a sample comprising between about 1500 to 7500 neutrophil cells/μL of blood.

A semi-quantitative determination may involve a determination whether or not the neutrophil level is "neutropenic". A "neutropenic" neutrophil level, may be defined as less than 1500 neutrophil cells/μL blood, preferably less than 1400, 1300, 1200, 1100 or 1000 cells/μL blood. A "neutropenic" CD16b level may be defined as the level typically found in a sample comprising less than 1500 neutrophil cells/μL blood, preferably less than 1400, 1300, 1200, 1100 or 1000 neutrophil cells/μL blood.

This may, for example, be equated to about <5 ng/mL CD16b which may, for example correspond to a cube unit reading of <25 CU.

A "neutropenic" lactate level may be defined as the level typically found in a sample comprising less than 1500 neutrophil cells/μL blood, preferably less than 1400, 1300, 1200, 1100 or 1000 neutrophil cells/μL blood.

A semi-quantitative determination may involve a determination whether or not the neutrophil level is "severely neutropenic". A "severely neutropenic" neutrophil level, which is a subset of the "neutropenic" level, may be defined as less than 1000 cells/μL blood, preferably less than 900, 800, 700, 600, 500, 400 or 300 cells/μL blood. A "severely neutropenic" CD16b level may be defined as the level typically found in a sample comprising less than 1000 neutrophil cells/μL blood, preferably less than 900, 800, 700, 600, 500, 400 or 300 neutrophil cells/μL blood. A "severely neutropenic" lactate level may be defined as the level typically found in a sample comprising less than 1000 neutrophil cells/μL blood, preferably less than 900, 800, 700, 600, 500, 400 or 300 neutrophil cells/μL blood.

A semi-quantitative determination may involve a determination whether or not the neutrophil level is "aberrantly high". An "aberrantly high" neutrophil level, may be defined as more than 7500 neutrophil cells/μL blood, preferably more than 7600, 7700, 7800, 7900, 8000, 8100, 8200, 8300, 8400, 8500 or 9000 cells/μL blood. An "aberrantly high" CD16b level may be defined as the level typically found in a sample comprising more than 7500 neutrophil cells/μL blood, preferably more than 7600, 7700, 7800, 7900, 8000, 8100, 8200, 8300, 8400, 8500 or 9000 cells/μL blood. An "aberrantly high" lactate level may be defined as the level typically found in a sample comprising more than 7500 neutrophil cells/μL blood, preferably more than 7600, 7700, 7800, 7900, 8000, 8100, 8200, 8300, 8400, 8500 or 9000 cells/μL blood.

In healthy subjects, the lactate level is typically about 1.0-1.5 mmol/L of blood. A semi-quantitative determination of the lactate level may involve a determination whether or not the lactate level is "normal", "elevated" or "aberrantly high", wherein a "normal" lactate level may be defined as about 1.0-1.5 mmol/L, an "elevated" lactate level may be defined as about 1.5-2.0 mmol/L and an "aberrantly high" lactate level may be defined as more than about 2.0 mmol/L, for example more than 2.5, 2.7, 3, 3.5, 3.7 or 4.0 mmol/L.

Thus, a CD16b level or neutrophil level below a predetermined threshold, such as a "neutropenic" or "severely neutropenic" level, may be indicative of neutropenia, neutropenic sepsis, a significant risk of developing neutropenia, and/or a significant risk of developing neutropenic sepsis. A CD16b level or neutrophil level above a predetermined threshold, such as a "neutropenic" level, may be indicative of the absence, or an insignificant risk, of the presence or development of neutropenia and/or neutropenic sepsis.

A CD16b level or neutrophil level above a predetermined threshold, such as an "aberrantly high" neutrophil level, may be indicative of (non-neutropenic) sepsis and/or a significant risk of developing (non-neutropenic) sepsis.

One or more appropriate thresholds may be used, preferably at least or exactly 2 or 3.

The CD16b level or neutrophil level may be used to predict, diagnose or exclude that the subject has, or is at significant risk of developing, neutropenia and/or neutropenic sepsis, or non-neutropenic sepsis.

In some embodiments, the method may comprise determining that the CD16b level is at or below the neutropenic or severely neutropenic threshold and, as a consequence of that determination, determining that the subject should receive an appropriate treatment for neutropenia and/or neutropenic sepsis. The method may further comprise a step of administering or adjusting a suitable treatment. Suitable treatments are discussed elsewhere herein, but in some circumstances, an appropriate treatment may be, or include, the reduction or discontinuation (which may be temporary) of a treatment that is causing neutropenia, such as chemotherapy.

In some embodiments, the method may comprise determining that the CD16b level is at or around the normal level, i.e. above the "neutropenic" threshold but below the "aberrantly high" threshold, and, as a consequence of that determination, determining that the subject does not require any treatment for neutropenia, neutropenic sepsis or (non-neutropenic) sepsis.

In some embodiments, the method may comprise determining that the CD16b level is at or below the neutropenic threshold but above the severely neutropenic threshold and, as a consequence of that determination, determining that the subject should be monitored, or continue to be monitored, for neutropenia and/or neutropenic sepsis.

In some embodiments, the method may comprise determining that the CD16b level is at or above the aberrantly high neutrophil threshold and, as a consequence of that determination, determining that the subject should receive an appropriate treatment for (non-neutropenic) sepsis. The method may further comprise a step of administering or adjusting a suitable treatment. Suitable treatments are discussed elsewhere herein.

The methods, systems, devices, testing kits or testing compositions of matter of the invention may be used in conjunction with monitoring other markers or indicators (such as symptoms) of neutropenia, neutropenic sepsis and/or (non-neutropenic) sepsis.

The subject is a mammalian subject, typically a human. The subject may, for example, be at significant risk of neutropenia, neutropenic sepsis and/or (non-neutropenic) sepsis; or be a subject suspected of suffering from neutropenia, neutropenic sepsis and/or (non-neutropenic) sepsis; or be a subject who has not been diagnosed as having, and/or is not known to have, neutropenia, neutropenic sepsis and/or (non-neutropenic) sepsis.

In some embodiments, the subject may have cancer. In some embodiments, the subject may be selected from a subject that (i) has been exposed to radiation; (ii) has received or is receiving a drug capable of causing neutropenia, such as an anti-psychotic drug or a thyroid drug; (iii) is suffering from HIV, hepatitis and/or an autoimmune disorder such as rheumatoid arthritis; (iv) has received or is receiving chemotherapy and/or radiotherapy; (v) is displaying or experiencing symptoms of an infection; and/or (vi) has recently undergone surgery.

Any such exposure, condition or treatment is preferably ongoing or took place within the last 1, 2, 3, 4, 5, or 6 weeks or months.

Thus, in some embodiments, the subject has cancer and has received or is receiving chemotherapy and/or radiotherapy and the method is carried out to detect, diagnose or monitor neutropenia and/or neutropenic sepsis.

It should be noted that the invention is performed in vitro based upon isolated samples, which may or may not have been pre-treated. The methods of the invention therefore typically do not (although they may) include steps of obtaining a sample for testing and are instead carried out on a provided sample. The sample may advantageously be obtained, or provided from, a fingerstick. This is particularly advantageous from a compliance perspective and provides adequate volume for the various testing devices described herein, in particular the lateral flow formats. Similarly, in some embodiments, the systems and test kits include suitable vessels for receiving a sample. The container may be coloured to protect any light sensitive analytes.

The blood sample may be a capillary or intravenous blood sample, preferably capillary, such as a blood sample obtained via a fingerstick (i.e. a small prick to the finger to draw one or a few drops of blood). Preferably, the sample is fresh, for example the sample may be analysed within 1, 2, 3, 4, 5, 10, 20, 30, 40, 40 or 60 minutes of the sample being taken, most preferably within 20 minutes or less, 10 minutes or less, 5 minutes or less or 1 minute or less.

In some embodiments, there is provided a point-of-care (POC) measurement of status of a subject with regard to neutropenia, neutropenic sepsis and/or non-neutropenic sepsis using a fingerstick test and lateral flow assay. The determination of CD16b conveniently avoids the need to perform a neutrophil count which is technically challenging and not well-suited for a point-of-care diagnostic test. The subject may be hospitalised or non-hospitalised.

Thus, any of the provided methods are preferably implemented in a system, device, composition of matter or test kit for a point of care setting, to be used e.g. by the patient, a nurse, clinician or other care provider.

The determination of the presence or level of a marker, such as CD16b, may rely upon a detection moiety, which may, e.g., be a binding reagent that binds specifically to the marker of interest (e.g. CD16b). Preferably, the level of CD16b is determined using one or more CD16b detection moieties, preferably labelled binding reagents, preferably one or more CD16b-binding antibodies. The binding reagent may for example be an antibody or aptamer. The antibody may be of monoclonal or polyclonal origin. Preferably, the antibody is a polyclonal antibody. Fragments and derivative antibodies may also be utilised, to include without limitation Fab fragments, scFv, single domain antibodies, nanoantibodies, heavy chain antibodies, aptamers etc. which retain specific binding function and these are included in the definition of "antibody". Such antibodies are useful in the methods, systems and test kits of the invention.

CD16b specific antibodies are commercially available, such as anti-CD16b antibody [MM0272-5L11] (ab89207) from Abcam Plc of Discovery Drive, Cambridge Biomedical Campus, Cambridge, CB2 0AX, UK. Most preferably, the antibody is anti-CD16 Human Fc gamma RIIIA/B (CD16b) Antibody (Polyclonal Goat IgG) from R&D Systems (Product code: AF 1597) or anti-Human CD16b Rabbit Antibody from Stratech Scientific Ltd (Product code: 11046-RP02). The antibody may be an anti-Human CD16 Rabbit Antibody.

Methods for generating specific antibodies are known to those skilled in the art. Antibodies may be of human or non-human origin (e.g. rodent, such as rat or mouse) and be humanized and/or otherwise modified according to known techniques (Jones et al., Nature (1986) May 29-June 4; 321(6069):522-5; Roguska et al., Protein Engineering, 1996, 9(10):895-904; and Studnicka et al., Humanizing Mouse Antibody Frameworks While Preserving 3-D Structure. Protein Engineering, 1994, Vol. 7, pg 805).

In certain embodiments the level of a marker, such as CD16b, is determined using an antibody or aptamer conjugated to a label. By label is meant a component that permits detection, directly or indirectly. For example, the label may be an enzyme, optionally a peroxidase, or a fluorophore. Coloured particles, such as gold labels may be utilised, e.g. in the form of colloidal gold.

Alternatively or additionally, a polystreptavidin-biotin system could be utilised to detect CD16b. In these embodiments, anti-CD16b binding antibodies may be conjugated to biotin. Biotinylated antibodies can bind to a polystreptavidin test line in a test device immobilising CD16b (if present). These antibodies can, optionally, further or alternatively comprise a detectable label, e.g. a gold label. In this embodiment, the detectable, e.g. gold, label facilitates detection of CD16b on the test strip. In a particular embodiment, the detection method employs two different anti-CD16b antibodies. In this embodiment, one of the anti-CD16b antibodies is conjugated to biotin, whereas the other anti-CD16b antibody is conjugated to a detectable label, e.g. gold label.

Biotin and streptavidin may alternatively be reversed, such that the anti-CD16b agent is conjugated to streptavidin and the test line comprises biotin.

Coloured particles, such as gold labels, may be detected optically and typically do not require the use of a detection agent. However, the detection of a label may require the use of a detection agent. Where the antibody is conjugated to an enzyme as the label, the detection agent may comprise a chemical composition such that the enzyme catalyses a chemical reaction to produce a detectable product. The products of reactions catalysed by appropriate enzymes can be, without limitation, fluorescent, luminescent, or radioactive or they may absorb or reflect visible or ultraviolet light. Examples of detectors suitable for detecting such detectable labels include, without limitation, x-ray film, radioactivity counters, scintillation counters, spectrophotometers, colorimeters, fluorometers, luminometers, photodetectors and densitometers. In certain embodiments, the detection agent may comprise a secondary antibody. The marker level is then determined using an unlabelled primary antibody that binds to the target protein, such as CD16b, and a secondary antibody conjugated to a label, wherein the secondary antibody binds to the primary antibody.

Additional techniques for determining expression level at the level of protein and/or the amount and/or concentration of a marker include, for example, Western blot, immunoprecipitation, immunocytochemistry, mass spectrometry, ELISA and others. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies. Levels of protein may be detected using a lateral flow assay in preferred embodiments.

The "sample" in or from which the CD16b is detected may be blood or a blood derivative containing neutrophils, such as plasma or buffy coat, preferably blood. The sample may have been pre-treated, for example through the addition of a stabiliser and/or anticoagulant, but in some embodiments the sample is not pre-treated. The method may include a step of removing one or more non-target cell types, or it may be carried out on a sample from which one or more non-target cell types have been removed. Exemplary non-target cells are erythrocytes. Non-target cells may be removed through physical means, such as a Histopaque™ gradient, or through other means, such as the use of binding reagents that specifically bind to a target molecule expressed on the surface of the non-target cells (and preferably not expressed, or not expressed in significant amounts on the surface of neutrophils). As mentioned above, the method may include a step of removing the soluble form of CD16b or it may be carried out on a sample from which the soluble form of CD16b has been removed. The method may include a step of lysing the neutrophils, or it may be carried out on a sample in which the neutrophil cells have been lysed.

The invention may be performed in lateral flow or vertical flow devices in certain embodiments. Generally, therefore, the invention (or one or more detection devices) may rely upon some form of solid support. The solid support may define a liquid flow path for the sample. In specific embodiments, the solid support comprises a chromatographic medium or a capillary flow device. The invention may be provided in a test strip format in some embodiments.

A suitable lateral flow configuration is shown schematically in FIG. 8. It comprises a sample pad (1) to which the sample may be added; a conjugate pad (2) which may contain detection moieties (3) such as labelled binding reagents; a suitable membrane, such as nitrocellulose, comprising a test capture line (5a) and optionally a control capture line (5b); and optionally an absorbent pad (6). These components may be assembled on a backing material, such as a plastic adhesive backing card. Preferably, the sample comprises filtered and/or washed cells (e.g. neutrophils).

A suitable lateral flow device may comprise:

a. a first test strip comprising a first sample application zone to which a sample from a subject is added, wherein the first sample application zone comprises a filter that traps white blood cells (e.g. neutrophils) and preferably does not trap the soluble form of CD16b and red blood cells;

b. a second test strip comprising:
  i. a second sample application zone to which the filter with trapped cells is added or with which the filter is otherwise brought into contact with;
  ii. a conjugate zone comprising at least one labelled detection moiety which binds to CD16b;
  iii. a solid support defining a liquid flow path for the sample and comprising (i) a test line for at least CD16b, the test line comprising an immobilised further detection moiety that also binds to CD16b thereby immobilising the CD16b at the test line to produce a signal via the labelled detection moiety also bound to the CD16b; or (ii) a test line for at least CD16b, the test line comprising an immobilised further detection moiety that binds to the CD16b-bound labelled detection moiety of step ii. thereby immobilising it at the test line producing a signal; and optionally further comprising:
  iv. at least one labelled control binding reagent that binds to a binding partner immobilised at a control line downstream of the test line for the CD16b and thus confirms that the test has completed successfully; and optionally further comprising:
  v. an absorbent material downstream of the test (and control, where present) lines to absorb excess sample.

The first test strip may comprise a zone in which lactate is detected and/or the level of lactate is determined. An exemplary format is shown in FIG. 12. The first test strip may be configured to perform a lactate assay that may be based on the enzymatic activity of lactate dehydrogenase.

Thus, the lactate assay may rely on lactate dehydrogenase enzyme a dye such as a yellow tetrazole (3-(4,5-dimethyl-thiazol-2-yl)-2, 5-diphenyltetrazolium bromide (MTT)) which can be converted to a purple precipitate called Formazan ((E, Z)-5-(4, 5-dimethylthiazol-2-yl)-1, 3-diphenyl-formazan) in the presence of lactate through the reduction of NAD+ to NADH during its conversion to pyruvate. The skilled person is aware that other reagents can be used in the assay to form different formazans. Dye formation may be assessed visually or measured via other means.

Thus, for example, the test strip may comprise, e.g. in immobilised form, lactate dehydrogenase and a dye in the form of a yellow tetrazole (3-(4,5-dimethylthiazol-2-yl)-2, 5-diphenyltetrazolium bromide (MTT)).

Prior to assaying the lactate concentration, the sample may be filtered to remove red blood cells. For example, the sample application pad may trap red blood cells and allow components such as lactate to travel to the detection zone.

For example, the sample may be applied to a first filter to trap white blood cells; the components not tapped by the first filter may be applied to a second filter to trap red blood cells, such that the lactate levels may be determined in a sample that is free of any cells.

In use, the sample containing unknown concentrations of analyte may be applied to the sample pad and travel to the conjugate pad where the analyte binds to the detection moiety and travels up the nitrocellulose membrane towards the capture lines. The test line comprises an immobilised binding reagent specific for the target analyte. If present in the sample, the analyte (bound to the detection moiety) will form a complex with immobilised binding reagent resulting in a visible test line. The control line, if present, comprises an immobilised binding reagent specific for a labelled control reagent. A visible label at the control line confirms that the test has run successfully. The presence and amount of label at the capture line(s) may be determined by eye or using a suitable lateral flow device reader such as the Cube (Optricon, Germany).

The testing device, kit, system or composition of matter can be of any form suitable for home use or use in a primary care setting (e.g. clinic). In specific embodiments, the testing device, kit, system or composition of matter may comprise a disposable single use device to which the sample is applied. Typically, it may comprise a sample application zone to which the sample is added. Generally, the sample application zone can receive an appropriate volume of sample, for example the volume of one or more drops of blood. The device, kit, system or composition of matter typically also incorporates a solid support which defines a liquid/capillary flow path for the sample once applied to the sample application zone. This may be a microfluidic flow-path. The sample application zone may be an integral part of the solid support. The solid support may comprise a chromatographic medium, such as a membrane material, which may preferably be nitrocellulose. A blood sample applied to the sample application zone will typically rehydrate the necessary reagents to detect the marker (such as CD16b). A chase fluid (diluent) may also be applied depending on the viscosity of the sample. The reagents may include a detection moiety such as a binding reagent which specifically interacts with the marker, such as with CD16b, or a substrate for effector molecules where activity is measured. A further reagent may be immobilized further along the flow path. This reagent may bind to the complex of marker and binding reagent. The binding reagent is typically labelled to provide a signal at the site of immobilization of the complex of marker and binding reagent (through binding to the further reagent). Suitable labels include fluorescent labels, magnetic labels, latex or gold as would be readily understood by one skilled in the art.

The binding reagent and further reagent are typically antibodies (as defined herein). Thus, in specific embodiments, the device, kit, system or composition of matter may comprise a lateral flow test strip.

The device, kit, system or composition of matter may also include a control zone to confirm sample has passed through the device satisfactorily. In the absence of confirmation by the control zone, the device, kit, system or composition of matter may indicate an invalid result to the user, for example via the display. The device, kit, system or composition of matter may act as a competitive or sandwich assay, as discussed herein. ELISA (enzyme linked immunosorbent assay) is an example of a suitable assay format that may be incorporated in the testing device used in the invention. Again, typically all reagents to detect the levels of the one or more markers are pre-loaded onto the device, kit, system or composition of matter such that they can interact with the blood sample once added to the device. This minimizes intervention and thus error caused by the subject. Thus, effectively, device, kit, system or composition of matter may only require the user to apply the sample and subsequently observe the output of the assay.

The device, kit, system or composition of matter may incorporate a suitable reader to provide a quantitative output (in conjunction with a processor and storage medium). This output can be an absolute or a relative output. Suitable readers may incorporate an illuminator to expose the device to a specific wavelength or wavelengths of light and a suitable detector for the reflected or emitted light. The device, kit, system or composition of matter may also incorporate a suitable processor and computer application to output the determined CD16b or neutrophil level based upon the detected signal. Thus, the processor running the computer application will be in operable connection with the reader. By "operable connection" is meant a functional connection that permits the exchange of a signal or information between the elements. An example of such a reader is the opTricon® 'Cube' reader (opTricon Gmbh). Others include the ESEQuant LR3 reader (Qiagen) and the Lumos reader (Lumos). Alternatively, in some embodiments the suitable processor and computer application to output the determined CD16b or neutrophil level based upon the detected signal may be incorporated on a remote computing device (e.g. tablet, phone or computer), which is in operable connection with the processor/computer application housed in the reader. This may take the form of a connectivity platform based, for instance, on cloud-based computing services. Thus, the output of the selected treatment based upon the detected signal may be displayed on a suitable display module (e.g. tablet, phone or computer) which is in remote connection (e.g. Wireless Internet connection, Bluetooth or any other Near Field Communication connection) with the processor/computer application of the reader. One example of such is LumiraDx Connect (LumiraDx). Thus, the processor/computer application housed in the reader may be configured to determine the levels of the markers on the device, kit, system or composition of matter and transmit the data to a remote computing device (e.g. tablet, phone or computer) which is configured to analyse the data and output the determined levels. In other embodiments, the data may be transmitted to a remote computing device (e.g. tablet, phone or computer) via a cloud-based computing service.

The device, kit, system or composition of matter may comprise one or more specific binding reagents to bind to the marker whose level is detected in the blood sample. As discussed above, where protein levels are measured the reagent may comprise an antibody (to include derivatives, fragments and aptamers).

The methods provided herein may comprise a step of determining (e.g. on the basis of the CD16b levels) that the subject is in need of a suitable treatment and/or a step of administering a suitable treatment. A suitable treatment may comprise or consist of one or more antibiotics. The antibiotic is preferably a broad-spectrum antibiotic, or a mixture of 2 or more antibiotics. Suitable antibiotics include macrolides (e.g. azithromycin, clarithromycin), cephalosporins (e.g. cefuroxime, cefpodoxime, cefdinir), ketolides (e.g. telithromycin), fluoroquinolones (e.g. moxifloxacin, gemifloxacin, levofloxacin), doxycycline, trimethoprim/sulfamethoxazole and amoxicillin/clavunate. These may be combined with one or more other treatments as appropriate.

As shown in the Examples, the inventors have demonstrated that a successful assay could be established for the measurement of recombinant CD16b in buffer when a combination of polyclonal antibody AF1597 was deposited on the Nitrocellulose at 1 mg/mL and also conjugated to gold at 30 μg/mL. Through optimisation of the system, an assay range of 10-1,000 ng/mL was achieved.

The system was then progressed to evaluate matrix effects using plasma to see if the assay would spike and recover in a simpler matrix than whole blood. The results showed that the test system could measure CD16b in plasma and gave a curve from 50-1,000 ng/mL.

Buffy coat preparations were then investigated using a histopaque gradient separation method, whereby blood is separated into erythrocytes and a plasma/cells mix which could be further processed in order to gain a reproducible white blood cell preparation. These cells were investigated neat and with the addition of lysis/solubilisation buffer and it was shown that the assay signal would increase with lysis indicating the release of "intracellular" CD16b from the cells.

Further experiments were conducted using five blood donors to determine if a correlation could be found between the CD16 levels of isolated and lysed neutrophils and the number of neutrophils counted by flow cytometry. The cells were processed and concentrated to give a range of cells (2×, neat and ½) which were assayed and measured by flow cytometry. The correlation of the neutrophil count with cellular CD16b (cube units for lysed cells) showed a $R2=0.861$, which is a good correlation.

It should be noted that throughout the specification the term "comprising" is intended to represent open-ended (i.e. including) language. However, for the avoidance of doubt, wherever the term "comprising" is used it is envisaged that the corresponding feature may be limited to that specified (i.e. consisting) as necessary.

Further aspects and embodiments of the invention are set out in the following clauses:

1. Use of CD16b as a marker for neutrophils in a sample, wherein the CD16b is detected and/or the level of CD16b is determined.

2. A method of detecting CD16b in a sample, the method comprising detecting CD16b, and/or determining the level of CD16b.

3. A method of detecting neutrophils and/or determining the neutrophil level in a sample, the method comprising detecting CD16b, and/or determining the level of CD16b.

4. A method for predicting, diagnosing, excluding and/or monitoring neutropenia and/or sepsis in a subject, the method comprising detecting CD16b, and/or determining the level of CD16b, in a sample.

5. A method or use according to any preceding clause, wherein the CD16b is detected and/or the level of CD16b is determined via a lateral flow assay.

6. A method or use according to any preceding clause, wherein the CD16b level is indicative of the neutrophil level in the sample.

7. A method or use according to any preceding clause, wherein the CD16b comprises, consists essentially of, or consists of the membrane-anchored form of CD16b (more particularly glycosylphosphatidylinisotol (GPI) anchored CD16b) and/or the intracellular form of CD16b, preferably wherein the CD16b predominantly comprises, consists essentially of, or consists of the membrane-anchored form of CD16b and the intracellular form of CD16b.

8. A method or use according to any preceding clause, wherein the CD16b is detected and/or the level of CD16b is determined, using one or more CD16b-specific detection moieties, preferably binding reagents, preferably one or more CD16b-specific antibodies.

9. A method or use according to clause 8, comprising the use of at least a first labelled binding reagent which specifically binds to CD16b and at least a second binding reagent that also specifically binds to CD16b, wherein the second binding reagent is preferably immobilised.

10. A method or use according to clause 9, wherein the label is gold, preferably colloidal gold.

11. A method or use according to any preceding clause, wherein a semi-quantitative or quantitative determination of the neutrophil level in the sample is made.

12. A method or use according to any preceding clause, wherein the neutrophil level is determined to be above or below one or more predetermined thresholds, preferably wherein (i) a neutrophil level below a predetermined threshold is indicative of neutropenia, neutropenic sepsis, a significant risk of developing neutropenia, and/or a significant risk of developing neutropenic sepsis;

(ii) a neutrophil level above a predetermined threshold is indicative of the absence, or an insignificant risk, of the presence or development of neutropenia and/or neutropenic sepsis;

(iii) a neutrophil level above a predetermined threshold is indicative of (non-neutropenic) sepsis or a significant risk of developing (non-neutropenic) sepsis; or (iv) a neutrophil level below a predetermined threshold is indicative of the absence, or an insignificant risk, of the presence or development of (non-neutropenic) sepsis.

13. A method or use according to clause 12, wherein one or more thresholds are used, wherein the threshold are selected from (a) less than 1000 neutrophil cells/μL blood, which is indicative of neutropenia, neutropenic sepsis, a significant risk of developing neutropenia and/or a significant risk of developing neutropenic sepsis;

(b) 1000-1500 neutrophil cells/μL blood, which is indicative of a need further to monitor the subject for the development neutropenia and/or neutropenic sepsis;

(c) more than 1500 neutrophil cells/μL blood, which is indicative of the absence, or an insignificant risk, of the presence or development of neutropenia and/or neutropenic sepsis;

(d) more than 7500 neutrophil cells/μL blood, which is indicative of (non-neutropenic) sepsis, or a significant risk of developing (non-neutropenic) sepsis; and/or (e) less than 7500 neutrophil cells/μL blood, which is indicative of the absence of (non-neutropenic) sepsis, or an insignificant risk of presence or development of (non-neutropenic) sepsis, preferably wherein any of thresholds (a), (b) and/or (c) may be referred to as "neutropenic" thresholds and/or any of thresholds (d) and/or (e) may be referred to as "(non-neutropenic) sepsis" thresholds.

14. A method or use according to any preceding clause, wherein the neutrophil level is used to predict, diagnose or exclude that the subject has, or is at significant risk of developing, neutropenia, neutropenic sepsis, and/or sepsis.

15. A method or use according to any preceding clause, wherein the sample is from a subject at significant risk of neutropenia and/or neutropenic or non-neutropenic sepsis and/or a subject suspected of suffering from neutropenia and/or neutropenic or non-neutropenic sepsis.

16. A method or use according to any preceding clause, wherein the sample is from a subject who has not been diagnosed as having, and/or is not known to have, neutropenia and/or neutropenic or non-neutropenic sepsis.

17. A method or use according to any preceding clause, wherein the sample is from a subject having cancer and/or undergoing chemotherapy and/or radiotherapy.

18. A method or use according to any preceding clause, wherein the sample is from a subject who (i) has been exposed to radiation; (ii) has received or is receiving a drug capable of causing neutropenia, such as an anti-psychotic drug or a thyroid drug; (iii) is suffering from HIV, hepatitis and/or an autoimmune disorder such as rheumatoid arthritis; (iv) has received or is receiving chemotherapy and/or radiotherapy; (v) is displaying or experiencing symptoms of an infection; and/or (vi) has recently undergone surgery.

19. A method or use according to any preceding clause, wherein the sample is (i) from a subject who is hospitalised; or (ii) from a subject who is not hospitalised.

20. A method or use according to any preceding clause, wherein the sample is a blood sample, preferably a capillary blood sample, such as a fingerstick blood sample.

21. A method or use according to any preceding clause, wherein the method or use comprises a step of cell lysis prior to determining the level of CD16b, preferably using a surfactant, which may be ionic or non-ionic, such as Triton X-100.

22. A method or use according to any preceding clause, wherein the CD16b comprises the soluble form of CD16b.

23. A method or use according to clause 18, wherein a reference is used to correct for the presence of the soluble form of CD16b, thereby allowing a determination of the level of the membrane-anchored form of CD16b (more particularly glycosylphosphatidylinisotol (GPI) anchored CD16b) and/or the intracellular form of CD16b.

24. A method or use according to any one of clauses 1-21, wherein the CD16b does not comprise the soluble form of CD16b.

25. A method or use according to clause 24, wherein the soluble form of CD16b is removed from the sample, preferably by filtering the sample using a filter that allows the separation of neutrophils from soluble CD16b, for example by size exclusion and/or adsorption.

26. A method or use according to clause 25, wherein the removal takes place prior to a step of cell lysis.

27. A method or use according to any preceding clause wherein the method or use further comprises detecting one or more different markers indicative of the presence of sepsis in the sample.

28. A method or use according to any preceding clause wherein at least 2, 3, 4, 5, 6, 7, 8, 9 or 10 or more samples are taken from the subject at different times and CD16b is detected and preferably the levels of CD16b are determined.

29. A method or use according to clause 28 wherein the samples are taken every 6 to 24 hours, such as daily, or every 2, 3, 4, 5, 6, 7 or 14 days.

30. A method or use according to any preceding clause wherein a prediction of impending neutropenia and/or neutropenic sepsis, or of (non-neutropenic) sepsis, or a diagnosis of neutropenia and/or neutropenic sepsis, or of (non-neutropenic) sepsis, results in a decision to treat and/or treatment of the subject with an antibacterial agent, preferably broad-spectrum antibiotics.

31. A method of predicting responsiveness of a subject to treatment with an antibiotic and/or selecting a subject for treatment with an antibiotic comprising performing the method of any preceding clause and predicting responsiveness and/or selecting the subject for treatment where neutropenia and/or neutropenic sepsis, or (non-neutropenic) sepsis, is predicted or diagnosed.

32. A method of treating or preventing neutropenia and/or neutropenic sepsis, or (non-neutropenic) sepsis, comprising administering an antibiotic to the subject suffering from neutropenia and/or neutropenic sepsis, or (non-neutropenic) sepsis, wherein the subject displays, in a sample, an altered level of at least CD16b and/or wherein the subject has been selected for treatment by performing the method of any preceding clause.

33. An antibiotic for use in a method of treating or preventing neutropenia and/or neutropenic sepsis, or (non-neutropenic) sepsis, wherein the subject displays, in a sample, an altered level of at least CD16b and/or has been selected for treatment by performing the method of any one of any preceding clause.

34. The method of any one of clauses 30-32 or antibiotic for use of clause 33, wherein the antibiotic is administered intravenously and/or is selected from macrolides (e.g. azithromycin, clarithromycin), cephalosporins (e.g. cefuroxime, cefpodoxime, cefdinir), ketolides (e.g. telithromycin), fluoroquinolones (e.g. moxifloxacin, gemifloxacin, levofloxacin), doxycycline, trimethoprim/sulfamethoxazole and amoxicillin/clavunate.

35. A testing device, testing kit or testing composition of matter comprising:
   a. A sample receiving zone to which a sample from a subject is added
   b. A conjugate zone comprising at least one labelled detection moiety which specifically binds to CD16b
   c. A solid support defining a liquid flow path for the sample and comprising (i) a test line for at least CD16b, the test line comprising an immobilised further detection moiety that also specifically binds to CD16b thereby immobilising the CD16b at the test line to produce a signal via the labelled detection moiety also specifically bound to the CD16b; or (ii) a test line for at least CD16b, the test line comprising an immobilised further detection moiety that specifically binds to the CD16b-specific labelled detection moiety of step (b) thereby immobilising it at the test line producing a signal; and optionally further comprising:
   d. at least one labelled control binding reagent that binds to a binding partner immobilised at a control line downstream of the test line for the CD16b and thus confirms that the test has completed successfully; and optionally further comprising:
   e. An absorbent material downstream of the test (and control, where present) lines to absorb excess sample.

36. The testing device, testing kit or testing composition of matter of clause 35 wherein the sample receiving zone is proportioned to receive between 10 and 100 µl of blood, such as around 40 µl of blood.

37. The testing device, testing kit or testing composition of matter of any one of clauses 35-36 wherein the solid support comprises a chromatographic medium and/or a capillary flow device.

38. The testing device, testing kit or testing composition of matter of any one of clauses 35-37 which is a test strip.

39. A system or test kit for diagnosing or monitoring a subject, comprising:
   a. A testing device for determining levels of at least CD16b in a sample, preferably according to any one of clauses 35-38
   b. A processor; and
   c. A storage medium comprising a computer application that, when executed by the processor, is configured to:
      i. Access and/or calculate the determined levels of at least CD16b in the sample on the testing device
      ii. Calculate a test score from the levels of the at least CD16b in the sample, optionally including a comparison of the levels with one or more thresholds and/or CD16b levels determined at one or more earlier time points, to thereby predict or diagnose neutropenia and/or neutropenic sepsis, or (non-neutropenic) sepsis; and
      iii. Output from the processor the predicted or diagnostic result for the subject.

40. A method or use according to any one of clauses 1-30 wherein the method or use comprises the use of a lateral flow device kit or composition, preferably a lateral flow device kit or composition as defined in any one of clauses 35-39.

41. A method of detecting CD16b in a sample, the method comprising detecting CD16b, and/or determining the level of CD16b, using a lateral flow assay.

42. A method according to clause 41, comprising detecting neutrophils in a sample by detecting CD16b and/or determining the neutrophil level in a sample by determining the level of CD16b.

43. A method for predicting, diagnosing, excluding and/or monitoring neutropenia, neutropenic sepsis and/or non-neutropenic sepsis in a subject, the method comprising detecting CD16b, and/or determining the level of CD16b, in a sample.

44. A method according to any one of clauses 41-43, wherein the CD16b comprises, consists essentially of, or consists of the membrane-anchored form of CD16b and/or the intracellular form of CD16b, preferably wherein the CD16b predominantly comprises, consists essentially of, or consists of the membrane-anchored form of CD16b and the intracellular form of CD16b.

45. A method according to any one of clause 41-44, wherein the CD16b is detected and/or the level of CD16b is determined, using one or more CD16b-specific detection moieties, preferably labelled binding reagents, preferably one or more CD16b-specific antibodies.

46. A method according to any one of clauses 41-45, wherein the neutrophil level is determined to be above or below one or more predetermined thresholds, preferably wherein
   (i) a neutrophil level below a predetermined threshold is indicative of neutropenia, neutropenic sepsis, a significant risk of developing neutropenia, and/or a significant risk of developing neutropenic sepsis;
   (ii) a neutrophil level above a predetermined threshold is indicative of the absence, or an insignificant risk, of the presence or development of neutropenia and/or neutropenic sepsis;
   (iii) a neutrophil level above a predetermined threshold is indicative of (non-neutropenic) sepsis or a significant risk of developing (non-neutropenic) sepsis; or
   (v) a neutrophil level below a predetermined threshold is indicative of the absence, or an insignificant risk, of the presence or development of (non-neutropenic) sepsis.

47. A method according to clause 46, wherein one or more thresholds are used, wherein the threshold are selected from
   (a) less than 1000 neutrophil cells/µL blood, which is indicative of neutropenia, neutropenic sepsis, a significant risk of developing neutropenia and/or a significant risk of developing neutropenic sepsis;
   (b) 1000-1500 neutrophil cells/µL blood, which is indicative of a need further to monitor the subject for the development neutropenia and/or neutropenic sepsis;
   (c) more than 1500 neutrophil cells/µL blood, which is indicative of the absence, or an insignificant risk, of the presence or development of neutropenia and/or neutropenic sepsis;
   (d) more than 7500 neutrophil cells/µL blood, which is indicative of (non-neutropenic) sepsis, or a significant risk of developing (non-neutropenic) sepsis; and/or
   (e) less than 7500 neutrophil cells/µL blood, which is indicative of the absence of (non-neutropenic) sepsis, or an insignificant risk of presence or development of (non-neutropenic) sepsis.

48. A method according to any one of clauses 41-47, wherein the sample is from a subject who (i) has been exposed to radiation; (ii) has received or is receiving a drug capable of causing neutropenia, such as an antipsychotic drug or a thyroid drug; (iii) is suffering from HIV, hepatitis and/or an autoimmune disorder such as rheumatoid arthritis; (iv) has cancer and/or has received or is receiving chemotherapy and/or radiotherapy; (v) is displaying or experiencing symptoms of an infection; and/or (vi) has recently undergone surgery.

49. A method according to any one of clauses 41-48, wherein the method comprises a step of cell lysis prior to determining the level of CD16b, preferably using a surfactant, which may be ionic or non-ionic, such as Triton X-100.

50. A method according to any one of clauses 41-49, wherein the CD16b comprises the soluble form of CD16b.

51. A method according to clause 50, wherein a reference is used to correct for the presence of the soluble form of CD16b, thereby allowing a determination of the level of the membrane-anchored form of CD16b and/or the intracellular form of CD16b.

52. A method according to any one of clauses 41-49, wherein the CD16b does not comprise the soluble form of CD16b.

53. A method according to clause 52, wherein the soluble form of CD16b is removed from the sample, preferably wherein the removal takes place prior to a step of cell lysis.

54. A method according to any one of clause 41-53, wherein the method or use further comprises detecting one or more different markers indicative of the presence of (neutropenic or non-neutropenic) sepsis in the sample.

55. A method according to any one of clauses 41-54, wherein at least 2, 3, 4, 5, 6, 7, 8, 9 or 10 or more samples are taken from the subject at different times and CD16b is detected and preferably the levels of CD16b are determined, preferably wherein the samples are taken every 6 to 24 hours, such as daily, or every 2, 3, 4, 5, 6, 7 or 14 days.

56. A method according to any one of clauses 41-55, wherein a prediction of impending neutropenia and/or neutropenic sepsis, or of (non-neutropenic) sepsis, or a diagnosis of neutropenia and/or neutropenic sepsis, or of (non-neutropenic) sepsis, results in a decision to treat and/or treatment of the subject with an antibacterial agent, preferably broad-spectrum antibiotics.

57. A method of predicting responsiveness of a subject to treatment with an antibiotic and/or selecting a subject for treatment with an antibiotic comprising performing the method of any one of clauses 41-56 and predicting responsiveness and/or selecting the subject for treatment where neutropenia and/or neutropenic sepsis, or (non-neutropenic) sepsis, is predicted or diagnosed.

58. A method of treating or preventing neutropenia and/or neutropenic sepsis, or (non-neutropenic) sepsis, comprising administering an antibiotic to the subject suffering from neutropenia and/or neutropenic sepsis, or (non-neutropenic) sepsis, wherein the subject displays, in a sample, an altered level of at least CD16b and/or wherein the subject has been selected for treatment by performing the method of any one of clauses 41-57.

59. An antibiotic for use in a method of treating or preventing neutropenia and/or neutropenic sepsis, or (non-neutropenic) sepsis, wherein the subject displays, in a sample, an altered level of at least CD16b and/or has been selected for treatment by performing the method of any one of clause 41-58.

60. The method of any one of clauses 56-58 or antibiotic for use of clause 59, wherein the antibiotic is administered intravenously and/or is selected from macrolides (e.g. azithromycin, clarithromycin), cephalosporins (e.g. cefuroxime, cefpodoxime, cefdinir), ketolides (e.g. telithromycin), fluoroquinolones (e.g. moxifloxacin, gemifloxacin, levofloxacin), doxycycline, trimethoprim/sulfamethoxazole and amoxicillin/clavunate.

61. A testing device, testing kit or testing composition of matter comprising:
   a. A sample receiving zone to which a sample from a subject is added
   b. A conjugate zone comprising at least one labelled detection moiety which specifically binds to CD16b
   c. A solid support defining a liquid flow path for the sample and comprising (i) a test line for at least CD16b, the test line comprising an immobilised further detection moiety that also specifically binds to CD16b thereby immobilising the CD16b at the test line to produce a signal via the labelled detection moiety also specifically bound to the CD16b; or (ii) a test line for at least CD16b, the test line comprising an immobilised further detection moiety that specifically binds to the CD16b-specific labelled detection moiety of step (b) thereby immobilising it at the test line producing a signal; and optionally further comprising:

d. at least one labelled control binding reagent that binds to a binding partner immobilised at a control line downstream of the test line for the CD16b and thus confirms that the test has completed successfully; and optionally further comprising:

e. An absorbent material downstream of the test (and control, where present) lines to absorb excess sample.

62. The testing device, testing kit or testing composition of matter of clause 61 wherein the solid support comprises a chromatographic medium and/or a capillary flow device.

63. The testing device, testing kit or testing composition of matter of clause 61 or 62, which is a test strip.

64. A system or test kit for diagnosing or monitoring a subject, comprising:

a. A testing device for determining levels of at least CD16b in a sample, preferably according to any one of clauses 61-63 b. A processor; and c. A storage medium comprising a computer application that, when executed by the processor, is configured to:

i. Access and/or calculate the determined levels of at least CD16b in the sample on the testing device ii. Calculate a test score from the levels of the at least CD16b in the sample, optionally including a comparison of the levels with one or more thresholds and/or CD16b levels determined at one or more earlier time points, to thereby predict or diagnose neutropenia and/or neutropenic sepsis, or (non-neutropenic) sepsis; and iii. Output from the processor the predicted or diagnostic result for the subject.

65. A method according to any one of clause 41-60 wherein the method comprises the use of a lateral flow device kit or composition, as defined in any one of clauses 61-64.

REFERENCES

Ning Jianga, Wei Chenb, Prithiviraj Jothikumara, Jaina M. Patelc, Rangaiah Shashidharamurthyc, II, Periasamy Selvarajc, and Cheng Zhua, b (2016). Effects of anchor structure and glycosylation of Fcγ receptor III on ligand binding affinity. Mol. Biol. of the Cell. 7; 27(22):3449-3458.

NICE 2012 Neutropenic sepsis: prevention and management in people with cancer. Clinical guideline CG151.

Zhang Y, Boesen C C, Radaev S, Brooks A G, Fridman W H, Sautes-Fridman C, et al. Crystal structure of the extracellular domain of a human Fc gamma RIII. Immunity. 2000; 13(3):387-95.

DESCRIPTION OF THE FIGURES

The invention will now be described by way of example with respect to the accompanying drawings in which:

FIG. 8 is a schematic of a typical lateral flow devide.

Figure 1:
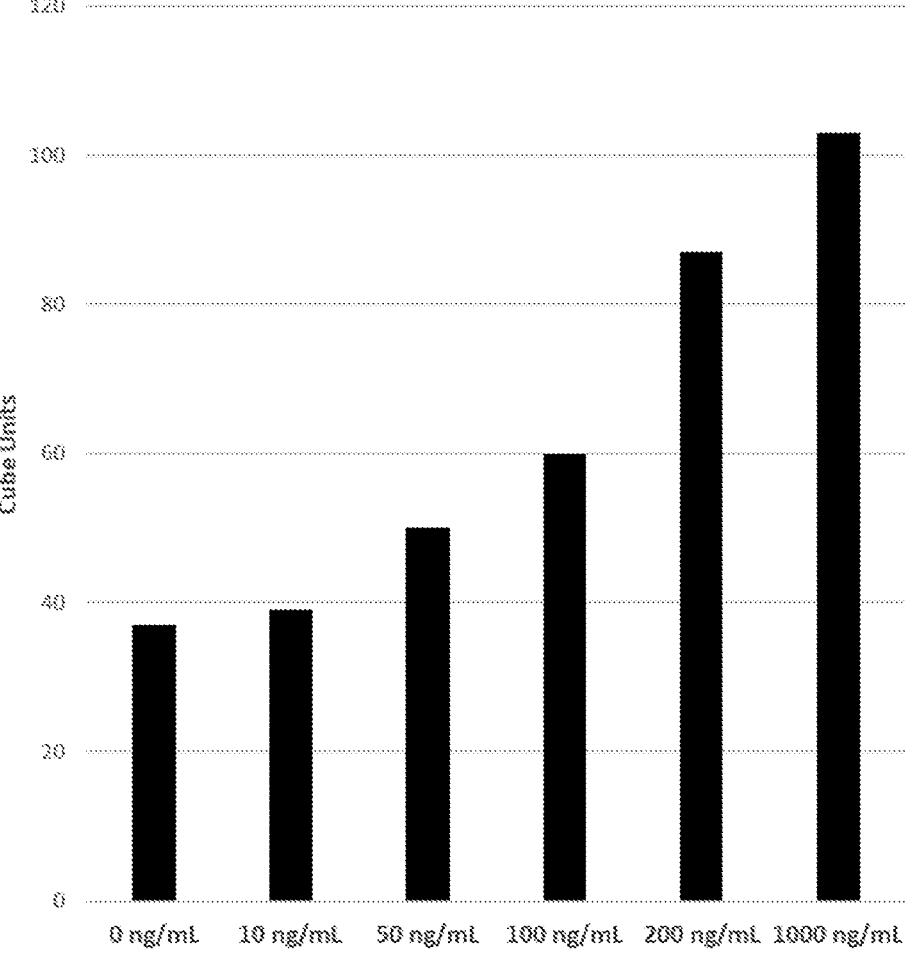
FIG. 1 is a bar graph to represent the change in test line measurement (cube units) for AF1597 deposited onto CN95 at 1 mg/mL (PBS+1% sucrose) with AF1597 conjugated to gold with varying concentrations of analyte spiked into plasma.

The invention will be further understood with reference to the following experimental Examples.

EXAMPLES

1. Materials and Methods
Reagents and Equipment

| Material | Supplier | Product Code |
| --- | --- | --- |
| FC gamma RIIIB/CD16b antibody (MM0272-5L11) | Novus-Biologicals | NBP2-12148 |
| α-CD16b Fc gamma RIIIB/CD16b Antibody | Novus-Biologicals | MM0272-5L11(Mab) NBP2-12148 |
| α-CD16b Human Fcy RIIIB/CD16b Antibody (Monoclonal Mouse IgG2 b) Clone #245514 | R&D Systems | MAB1597 |
| α-CD16b Human Fcy RIIIA/B (CD16b) Antibody (Polyclonal Goat IgG) | R&D Systems | AF 1597 |
| CD16b -Std Material Recombinant Human Fcy RIIIB/CD16b (aa18-200) | R&D Systems | 9948-FC-100 |
| α- Human CD16b Mouse MAB | Stratech Scientific Ltd | 11046-MM01 |
| α- Human CD16b Rabbit Antibody | Stratech Scientific Ltd | 11046 -RP02 |
| Goat- α-Mouse (10 mg/mL) | Lampire Biological Laboratories Ltd. | 7455507 |
| Goat- α-Rabbit (10 mg/mL) | Lampire Biological Laboratories Ltd. | 7455607 |
| CD16b-Std Material Recombinant Human Fcy RIIIB/CD16b (aa18-200) | R&D Systems | 9948-FC-100 |
| Recombinant Human Fc gamma RIIIB/CD16b Protein | R&D Systems | 1597-FC-050 |
| Recombinant Human Fey RIIIA/CD16a protein (Gly17-Gln208) | R&D Systems | 8894-FC |
| Human CD16b/FCGR3B Protein (His Tag, NA2 allotype) (Met 1-Ser 200) | Stratech Scientific Ltd | 11046-H08H |
| BSA | Sigma Aldrich | 1002740634 |
| Fatty acid Free BSA | Sigma Aldrich | A7030 |
| Rabbit-α-Goat (10 mg/mL) | Lampire Biological Laboratories Ltd. | 7457307 |
| Cell Extraction Buffer PTR-5X | Abcam | ab253215 # P3138 |
| Tween 20 | Sigma Aldrich | P1379 |
| PBS (tablets) | Sigma Aldrich | P4417 |
| PBST (PBS + 0.1% Tween 20) | Mologic | N/A |
| PBSTB(PBST + 1% BSA) | Mologic | N/A |
| PBSE(PBS + EDTA 1.8 mg/mL} | Mologic | N/A |
| 20 mM MES pH 5.5 | Mologic | N/A |
| Gold Drying Buffer (20 mM Taps pH 8.5 + 5% Sucrose + 3% BSA + I % Tween 20) | Mologic | N/A |
| 200 mg/mL aq. BSA | Mologic | N/A |
| 40 nm Gold (OD 5, OD 4.76) | BBI Solutions | EMGC40 |
| 1M Tris pH 9.4 | Mologic | N/A |
| 20 mM MES pH 6.5 | Mologic | N/A |
| 20 mM MES pH 6.7 | Mologic | N/A |
| 20 mM BES pH 6.9 | Mologic | N/A |
| 20 mM TES pH 7.1 | Mologic | N/A |
| 20 mM TES pH 7.5 | Mologic | N/A |
| 20 mM TES pH 7.8 | Mologic | N/A |
| 20 mM TAPS pH 8.5 | Mologic | N/A |
| 20 mM Borate pH 8.5 | Mologic | N/A |
| 20 mM Borate pH 9.0 | Mologic | N/A |
| 20 mM Borate pH 9.3 | Mologic | N/A |
| 1M NaCl | Mologic | N/A |
| 5%, 50% Sucrose | Mologic | N/A |
| α -Mouse IgG AP Conjugate | Sigma | A4102 |
| pNPP substrate | BioPanda | pNPP-001 |
| Vivaspin 500 | Sartorius | VS0121 |
| Biotinylation Lightning Link Kit | Expedeon | 701-0000 |
| Polystr eptavidin R | BioTez | K558-M |
| Streptavidin - HRP Conjugate | R&D Systems | Duo Set 893975 |
| TMB Substrate | Bio Panda | TMB-S-004 |
| Stop Reagent | Bio Panda | STP-001 |
| TBST (ELISA Wash Solution) | Mologic | SOP 321vl |
| Absorbent Pad/sink pad - 22 mm | Ahlstrom-Munksj | 535400669224 |
| Backing Card - 60 mm | Unisart | 33393619 |
| Conjugate Pad - 17 mm | Ahlstrom | Grade 8951 |
| Conjugate Pad- 17 mm | Ahlstrom | Grade 8980 |
| CN180 | Sartorius Stedtim | 500752766 |
| CN140-25 mm | Unisart | 500586972 |
| CN95 - 25 mm | Unisart | 500677182 |
| FR1 -10 mm | Mdi | R2990/998/1 |

-continued

| Material | Supplier | Product Code |
|---|---|---|
| Vivid Plasma Separation | Pall | 79EXPPA0200S0X |
| Cytosep 1660 | Ahlstrom-Munksjo | MHPM1660 |
| Triton x-100 | Sigma Aldrich | T9284 |
| 96 F well High bind plate | Costar | 9018 |
| 96 F well Low bind plate | Medline | 9000 11SP |
| Deionised water | ELGASystem | Mologic |
| 30 mL Polystyrene universal container | STARLAB | E1412-3011 |
| 1.5 mL Microcentrifuge tubes | STARLAB | S1615-5500 |
| 10 ml K2E(EDTA) Vacutainer | Becton Dickinson | 367525 |
| Histopaque | Sigma Aldrich | 10771 |
| LP3 tubes/Rohren tubes | Sarstedt, Inc | 55.484 |
| Rohren push cap lids | Sarstedt, Inc | 65.809 |
| 200 mM Tris | Mologic | N/A |
| 1-Methyl-1-piperidinomethane sulfonate | Sigma | M8640 |
| 3-(4,5-Dimethyl-2-thiazolyl)-2,5-diphenyl-2H-tetrazolium bromide | Sigma | M2128 |
| β-Nicotinamide adenine dinucleotide | Sigma | N8129 |
| Sodium-L-Lactate | Sigma/Aldrich | 71718 |
| L-Lactate dehydrogenase | Roche | 10127230001 |
| Cube reader | Optricon, Berlin | 875-1622-0016 |

Conjugation of CD16b Antibody to Gold Nanoparticles

Buffer Screening Test

The buffer type, molarity and pH can affect the antibody binding to the gold particles because the binding is largely due to the charge and hydrophobic interactions. To test a range of buffers, 20 mM buffers were made up at the pH ranging from 6.7 to 9.3

The antibody was loaded at 15 µg/mL for all buffers investigated. A volume of 1.5 µL antibody was added to the bottom of a clean 96 µlate well, 5 µL of conjugation buffer was then added and finally 100 µL of gold OD5. These are incubated for 10 minutes at room temperature whilst stationary. The plate was then read to measure absorbance using a plate reader at 550 and 600 nm; the ratio of 550/600 was then calculated to give an aggregation ratio. If the aggregation ratio was ≥3.5 then the buffer was deemed suitable for conjugation.

CD16b Antibody Loading Test

Once a suitable buffer had been chosen from above the optimal loading of the antibody was determined. The loading concentrations 0 µg/mL to 30 µg/mL in 5 µg/mL increments were investigated in the buffer of choice. The respective volume of antibody (0, 0.5, 1.0 µL etc. . . . ) were added to the bottom of a clean 96 well plate, 5 µL of conjugation buffer was added followed by 100 µL of OD5 gold. Again, these were incubated for 10 minutes at room temperature. Once incubated, 10 µL of 1M NaCl was placed into each well. If the gold was not sufficiently coated, then the concentrated salt causes the gold conjugate to become unstable and aggregate, indicated by a colour change from bright pink to purple/grey. To determine the degree of aggregation, the plate was read on a plate reader and, again, an absorbance of 550 and 600 nm was measured. The ratio of 550/600 was taken and if the conjugate again met an aggregation ratio of 3.5 then it was deemed suitable.

Conjugation of CD16b Antibody for the Assay

The conjugation of the antibody at 15 µg/mL was achieved by the following method:

Place 15 µL of 1 mg/mL antibody at the bottom of a clean 1.5 mL centrifuge tube

Then add 50 mL of conjugation buffer to the antibody

Add 1000 µL of OD 5 40 nm gold to the tube, lightly vortex, and then leave stationary for 10 minutes After 10 minutes, add 10 µL of 200 mg/mL BSA (aq.) and leave stationary for a further 30 minutes Place the tube into a suitable centrifuge and spin at 4000 g for 10 minutes Remove the supernatant and replace with the same volume of gold drying buffer The conjugation of the antibody at 20 µg/mL was achieved by the following method:

Place 20 µL of 1 mg/mL antibody at the bottom of a clean 1.5 mL centrifuge tube

Then follow steps 2-6.

The conjugation of the antibody at 30 µg/mL was achieved by the following method:

Place 30 µL of 1 mg/mL antibody at the bottom of a clean 1.5 mL centrifuge tube

Then follow steps 2-6.

Nitrocellulose Plotting

Three different NCs were plotted (CN95, CN140 and CN180) using the CD16b antibody of interest, these have differing pore sizes and hence run at different speeds. The antibody was prepared in PBS+1% Sucrose to a final concentration of between 0.5 mg/mL-1 mg/mL. The antibody was plotted in 10 cm bands and then dried at 37° C. for a minimum of 30 minutes. Strip Construction The antibody plotted onto NC bands were mounted on adhesive backing card at the base of the card. The absorbent pad/sink pad was mounted at the top of the backing card with a 7 mm overlap on the NC. These bands were then cut into 3 mm wide strips using the Biodot Guillotine Cutter.

The assay was run using the two following procedures:

'Wet' Assay:

1. Place 4 ml Gold Conjugate (ODS) into the well of a low bind microtitre plate and add 20 ml of sample or CD16b analyte in buffer (PBS).

2. Place the test strip into the well and allow to run until the well is empty.

3. Add 30 ml of chase buffer (PBST) and allow to run until the well is empty.

4. Place strip into a suitable holder and read the line values using an Optricon cube reader.

Isolated WBC Assay:

1. Place 4 µl Triton X-100 (0.482%) into the well of a low bind microtitre plate and add 28 µl of cell suspension and preincubate for 5 mins. (Final dilution of TX-100 is 0.125%)

(Lysed Cells)

2. Transfer 20 μl of lysed cell mixture from to a fresh well containing 4 μL Gold conjugate (ODS).

3. Proceed as from Step 2 using 'Wet' Assay protocol.

Blood Samples

Blood samples were taken from 13 anonymous donors at Mologic Ltd, in line with the Human Tissue Act license number 12647. These were used as required for the experiments, stored for no longer than two weeks and disposed of in line with Mologic's Code of Practice.

| Mologic Blood Donor Number | Volume/tube type |
|---|---|
| 1095 | 2x 10 mL/EDTA |
| 1079 | 2x 10 mL/EDTA |
| 1099 | 1x 10 mL/EDTA 1x |
| 1101 | 2x 10 mL/EDTA |
| 1103 | 1x 10 mL/EDTA 1x |
| 1104 | 1x 10 mL/EDTA 1x |
| 1105 | 1x 10 mL/Heparin |
| 1107 | 2x 10 mL/EDTA |
| 1109 | 2x 10 mL/EDTA |
| 1113 | 2x 10 mL/EDTA |
| 1114 | 2x 10 mL/EDTA |
| 1117 | 2x 10 mL/EDTA |
| 1118 | 2x 10 mL/EDTA |

Example 1 Initial Conjugation and Testing of Anti-CD16b Antibodies

Buffer Screening Test

The first experiments performed involved the conjugation of selected antibodies to gold nanoparticles with a buffer screen (at a set 15 μg/mL loading). 8 buffers were chosen to give the widest range of pH and buffer type. The antibodies that were tested were AF1597, Mab 1597 and NBP-2. When performing the buffer screen, the absorbance for the gold particles was read at 550 and 600 nm, a ratio of 550/600 nm was taken; if the ratio was found to be ≥3.5 then it met the criteria required to be suitable for conjugation. The results for this can be found in Table 1.

TABLE 1

Table to show the aggregation ratios for varying conjugation buffers at an antibody loading of 15/Ag/mL (15 μg/mL).
Aggregation Ratio 550/600 nm

| | MES 6.7 | BES 6.9 | TES 7.1 | TAPS 7.5 | TAPS 8.5 | Borate 8.5 | Borate 9.0 | Borate 9.3 |
|---|---|---|---|---|---|---|---|---|
| AF1597 | 3.2874 | 4.1212 | 3.9935 | 3.9126 | 4.2276 | 3.9040 | 4.0498 | 3.9773 |
| Mab1597 | 4.1444 | 1.4042 | 2.1059 | 1.9489 | 4.2687 | 2.1553 | 2.2187 | 2.5224 |
| NBP-2 | 4.5191 | 4.2500 | 4.0586 | 2.3903 | 4.3822 | 4.3011 | 4.1679 | 4.0334 |

As can be seen from Table 1, 7 of the 8 buffers tested gave an acceptable aggregation ratio for the AF1597 and NBP-2, plus 2 out of 8 were suitable for the Mab1597. The buffer that was chosen to take forward for conjugation was TAPS pH 8.5 as all three antibodies gave an aggregation ratio of >4.2. Once the gold conjugation conditions were established, batches of gold were made and all three were resuspended in gold drying buffer and tested on strips.

Initial Orientation Testing

The antibodies were then deposited onto nitrocellulose (NC, CN140) by placing a 1 μL drop of 1 mg/mL antibody in a solution of PBS+1% sucrose onto the NC. This allowed for an initial orientation experiment to be performed against the newly conjugated gold nanoparticles. These strips and gold particles are tested with a blank buffer (0 ng/mL PBS) and varying concentrations of recombinant CD16b analyte (in PBS). It should be noted that all 9 combinations of NC and gold were tested but only those combinations that gave a visible response are shown in Table 2.

TABLE 2

Raw data obtained for hand deposited antibodies (in PBS + 1% sucrose) on CN140 strips with varying gold conjugations at different concentrations of CD16b analyte.

| AB (CN140) | Gold (AB) | Concentration (ng/mL) | T |
|---|---|---|---|
| AF1597 | AF1597 | 0 | 1.5 |
| | | 10 | 6.3 |
| | | 100 | 32 |
| | | 1000 | 72 |
| Mab1597 | AF1597 | 1000 | 8.6 |
| NBP-2 | NBP-2 | 0 | 29 |
| | | 1000 | 59 |
| | Mab1597 | 0 | 41 |
| | | 1000 | 57 |
| | AF1597 | 1000 | 3 |

As can be seen from Table 2, when the AF1597 (AF) was on the NC and on the gold it gave the best curve response with a sensitivity of 100 ng/mL being seen.

When the Mab1597 (Mab) and NBP-2 were deposited on the NC and the AF1597 gold was tested, there was no response for a 1000 ng/mL sample. The NBP-2 on the NC and also on the gold showed a high non-specific interaction (spot seen for 0 ng/mL) and no real increase in signal for a 1000 ng/mL sample. The same response was seen when the NBP-2 was deposited on NC and the Mab1597 (Mab) was conjugated to the gold, with a high non-specific interaction seen and no increase in signal to a 100 ng/mL sample. There was some form of aggregation of the gold, which could be seen as a visible red line at the bottom of the NC. To confirm the orientation of the assay and to determine if the AF1597 self-pair was correct, small bands of antibody were deposited using a standard Isoflow machine to plot the antibody onto the NC (10 cm band). This gave a line response which could be more accurately read on the cube reader as opposed to a spot. Additionally, another monoclonal antibody (MM01) was also tested. The results for the Isoflow deposited antibodies can be found in Table 3.

TABLE 3

Raw data obtained for Isoflow deposited antibodies (in PBS + 1% sucrose) on CN140 strips with varying gold conjugations at two different concentrations of CD16b analyte.

| NC | Gold | 0 ng/mL | 1000 ng/mL |
|---|---|---|---|
| AF1597 | AF1597 | 3.1 | 91 |
| Mab1597 | AF1597 | 2 | 6 |
| NBP-2 | AF1597 | 3.6 | 17 |

TABLE 3-continued

Raw data obtained for Isoflow deposited antibodies (in
PBS + 1% sucrose) on CN140 strips with varying gold
conjugations at two different concentrations of CD16b analyte.

| NC | Gold | 0 ng/mL | 1000 ng/mL |
|---|---|---|---|
| AF1597 | Mab1597 | 2.6 | 31 |
| Mab1597 | Mab1597 | 45 | 71 |
| NBP-2 | Mab1597 | 110 | 156 |
| AF1597 | NBP-2 | 1.5 | 146 |
| Mab1597 | NBP-2 | 106 | 72 |
| NBP-2 | NBP-2 | 71 | 145 |
| AF1597 | MM01 | 1.6 | 4.8 |
| Mab1597 | MM01 | 47 | 29 |

As can be seen from Table 3, when the AF1597 was conjugated to the gold, the best specific signal (high CD16b test response with a low blank background) was seen when the AF1597 was deposited on the NC. It was therefore decided to continue with the development of the AF1597 pair system (using this antibody on both the test line and gold) as it showed the most reproducible results. To confirm the initial result, a buffer curve was run to determine assay sensitivity and range.

Development of AF1597 Self Paired System

Buffer Curve

To find the initial assay sensitivity and range, CD16b was spiked into PBS at 10, 100, 1,000 and 10,000 ng/mL and the hand deposited strips, Isoflow deposited antibody on the NC with old gold and Isoflow deposited antibody on the NC with new gold conjugates were investigated. The results for the buffer curve can be found Table 4.

TABLE 4

Raw data obtained for AF1597 antibody deposited by different
methods (in PBS + 1% sucrose) with two different
batches of gold and varying concentrations of analyte

| Concentration | Hand Plot | Isoflow/Gold (old batch) | Isoflow/Gold (new batch) |
|---|---|---|---|
| 0 | 1.5 | 4.3 | 3.1 |
| 10 | 6.3 | 4.3 | 25 |
| 100 | 32 | 46 | 59 |
| 1000 | 72 | 72 | 91 |

As can be seen from Table 4, the non-specifics for the AF1597 pair system are low for all three golds tested and all show a specific test line signal over the range tested. For the hand plotted antibody system, the 100 and 1,000 ng/mL gave specific signal; these signals were comparable when tested on the Isoflow plotted antibody system.

Fatty Acid Free BSA Vs. Normal BSA

An optimisation was attempted to see if a change of gold blocking agent could improve assay performance (gain in specific signal). For this, two forms of BSA were tested to block the gold conjugates, these were fatty acid free BSA and normal BSA. The results for the comparison can be found in Table 5.

TABLE 5

Raw data obtained for AF1597 antibody deposited on
CN95 (in PBS + 1% sucrose) with two different
blocking agents (fatty acid free and normal BSA) on
conjugated gold with varying concentrations of analyte.

| AB on CN95 | Gold (AB) | Concentration (in PBS) | T |
|---|---|---|---|
| AF1597 | AF1597 FaF BSA | 0 ng/mL | 3 |
| | | 10 ng/mL | 26 |

TABLE 5-continued

Raw data obtained for AF1597 antibody deposited on
CN95 (in PBS + 1% sucrose) with two different
blocking agents (fatty acid free and normal BSA) on
conjugated gold with varying concentrations of analyte.

| AB on CN95 | Gold (AB) | Concentration (in PBS) | T |
|---|---|---|---|
| | | 50 ng/mL | 73 |
| | | 100 ng/mL | 98 |
| | | 200 ng/mL | 107 |
| | AF1597 BSA | 0 ng/mL | 1.5 |
| | | 10 ng/mL | 27 |
| | | 50 ng/mL | 73 |
| | | 100 ng/mL | 129 |
| | | 200 ng/mL | 108 |

As can be seen from Table 5, the results for the two blocking agents were very comparable, with both giving a sensitivity of 10 ng/mL and increasing specific signal up to 100 ng/mL.

Increased Antibody Loading on Gold

The method for conjugating 15, 20 and 30 μg/mL to gold is described above. To determine the effect of a higher loading of the gold conjugates, the same concentrations of analyte were run again. The results for the higher loaded gold conjugates can be found in Table 6.

TABLE 6

Raw data obtained for AF1597 antibody deposited on
CN95 (in PBS + 1% sucrose) with two different
blocking agents (fatty acid free and normal BSA) on
conjugated gold with varying concentrations of analyte.

| | | Antibody loading on gold | | |
|---|---|---|---|---|
| NC | Concentration | 15 μg/mL | 20 μg/mL | 30 μg/mL |
| AF1597 | 0 ng/mL | 1.3 | 1.7 | 1.3 |
| on CN95 | 10 ng/mL | 5.4 | 6.2 | 15 |
| | 50 ng/mL | 47 | 54 | 41 |
| | 100 ng/mL | 96 | 86 | 84 |
| | 200 ng/mL | 94 | 110 | 100 |
| | 1000 ng/mL | 98 | 122 | 137 |

As can be seen from Table 6, the 20 μg/mL gold conjugate showed an increase in signal for all concentrations tested when compared to the 15 μg/mL coat; the lowest increase in specific signal was seen between 200 and 1,000 ng/mL. This suggested the higher gold loading gave an improvement in the assay performance by giving a larger range to the assay. This was more apparent when the 30 μg/mL coat was tested, with a specific signal gain at both the low end (10 ng/mL) and an enhanced specific signal gain between 200 and 1,000 ng/m L. This suggested that the best gold conjugate loading concentration at this stage was 30 μg/mL.

Increasing Test Line Antibody Concentration

As seen above, an increase in antibody loading on the gold conjugate gave a better assay response. To investigate if this could be improved further, the antibody deposited onto the test line was also increased. The test line antibody concentrations investigated were the current 1.0 mg/mL along with 1.5 and 2.0 mg/mL, using the 30 μg/mL gold conjugate; the results are displayed in Table 7.

TABLE 7

Raw data obtained for AF1597 antibody deposited on CN95 (in PBS + 1% sucrose)
at varying concentrations with increasing concentrations of CD16b analyte.

| | | Test Line Concentration | | | | |
| NC (AB) | Concentration | 13/1 - 1 mg/mL | 14/1 - 1 mg/mL | 15/1 - 1 mg/mL | 15/1 - 1.5 mg/mL | 15/1 - 2.0 mg/mL |
| --- | --- | --- | --- | --- | --- | --- |
| CN95 | 0 ng/mL | 1.3 | 3.2 | 2.1 | 1.6 | 2 |
| (AF1597) | 10 ng/mL | 15 | 19 | 26 | 18 | 19 |
| | 50 ng/mL | 41 | 78 | 93 | 53 | 77 |
| | 100 ng/mL | 84 | 90 | 107 | 98 | 88 |
| | 200 ng/mL | 100 | 134 | 148 | 118 | 121 |
| | 500 ng/mL | — | — | 153 | 114 | 133 |
| | 1000 ng/mL | 137 | 135 | 144 | 107 | 135 |

As can be seen from Table 7, the 1 mg/mL data showed the best response and was very comparable to the previous results obtained. The results suggested that there was enough antibody in the system at 1 mg/m L. As there was no benefit at this stage of increasing the antibody concentration, it was decided to keep the current system with 1.0 mg/mL being deposited on the test line.

Change of Nitrocellulose

Another change that can improve assay sensitivity and range of a lateral flow assay is the NC membrane used. The majority of the development work had been performed on CN95, so two other NCs were investigated to see if the assay sensitivity and range could be improved. The CN140 and CN180 NCs are slower running membranes with smaller pores and can give increased sensitivity and range by allowing more binding event complexes to be formed on the test line.

TABLE 8

Raw data obtained for AF1597 antibody deposited on CN95,
CN140 and CN180 (in PBS + 1% sucrose) with AF1597
conjugated to gold with varying concentrations of analyte.

| | | Nitrocellulose Type | | | |
| Antibody | Concentration | CN95 (13/1) | CN95 | CN140 | CN180 |
| --- | --- | --- | --- | --- | --- |
| AF1597 | 0 ng/mL | 1.3 | 3.2 | 3.2 | 2.2 |
| (1 mg/mL) | 10 ng/mL | 15 | 19 | 13 | 21 |
| | 50 ng/mL | 41 | 78 | 74 | 70 |
| | 100 ng/mL | 84 | 90 | 89 | 92 |
| | 200 ng/mL | 100 | 134 | 100 | 95 |
| | 1000 ng/mL | 137 | 135 | 104 | 99 |

As can be seen from Table 8, the best results were obtained when CN95 was used as the NC and these results were very comparable to the previous data obtained with the same NC. Whilst giving good specific signal for all concentrations, the CN140 and CN180 gave lower specific signal for both 200 and 1,000 ng/mL. Between 10 and 200 ng/mL, the three NCs gave very comparable specific signal, this suggested that there was no benefit to changing the NC at this stage.

The system taken forward for testing in plasma and blood samples was CN95 with 1 mg/mL AF1597 antibody deposited in PBS+1% sucrose and AF1597 loaded at 30 μg/mL on gold.

Example 2—Detection of CD16b in Spiked Samples

Spiked Plasma Curve

It was decided initially to see if the CD16b could be spiked and recovered in a simpler matrix than blood. The matrix chosen for this was plasma, with whole blood being drawn and collected in EDTA and lithium heparin tubes. Once collected, the blood was spun down at 1,228x g for 10 minutes, the blood separates into three distinct layers at this point; plasma, buffy coat and erythrocytes. The plasma was collected from the top layer and placed into polypropylene tubes. The analyte (CD16b) was then spiked in the plasma and run on the strips to see if it could be recovered successfully; the results for this experiment can be found in Table 9 and FIG. 1.

TABLE 9

Raw data obtained for AF1597 antibody deposited on CN95
with varying concentrations of CD16b analyte spiked
into either EDTA or lithium heparin collected plasma.

| NC (AB) | Gold (A/B) | Anticoagulant | Concentration CD16b in Plasma | T |
| --- | --- | --- | --- | --- |
| CN95 | AF1597 | EDTA | 0 ng/mL | 37 |
| (AF1597 1 | (30 μg/mL) | | 10 ng/mL | 39 |
| | | | 50 ng/mL | 50 |
| | | | 100 ng/mL | 60 |
| | | | 200 ng/mL | 87 |
| | | | 1000 ng/mL | 103 |
| CN95 | AF1597 | Lithium | 0 ng/mL | 13 |
| (AF1597 1 | (30 μg/mL) | | 100 ng/mL | 34 |
| | | | 1000 ng/mL | 55 |

As can be seen from Table 9 and FIG. 1, there was specific signal gained for 50-1,000 ng/mL CD16b in EDTA plasma (plus a signal was also obtained for 100 and 1,000 ng/mL CD16b in lithium heparin collected plasma). The EDTA plasma showed greater specific signal differential for the CD16b concentrations measured, suggesting it was the better anticoagulant to collect the venous blood.

If fingerstick whole blood is used there may not be a need for an anticoagulant collection method in the final form. It was also noticed that there was some endogenous the soluble form of CD16b in the plasma of the blood sample taken. This is not surprising as neutrophils are known to shed CD16b as part of their turnover in blood. The neutrophils can be found in the buffy coat layer of the blood sample that has been spun down. To investigate the measurement of cellular CD16b, buffy coat isolation is required. This can then be evaluated in the assay, utilising detergent lysis/solubilisation to release any cellular CD16b present.

Figure 2:
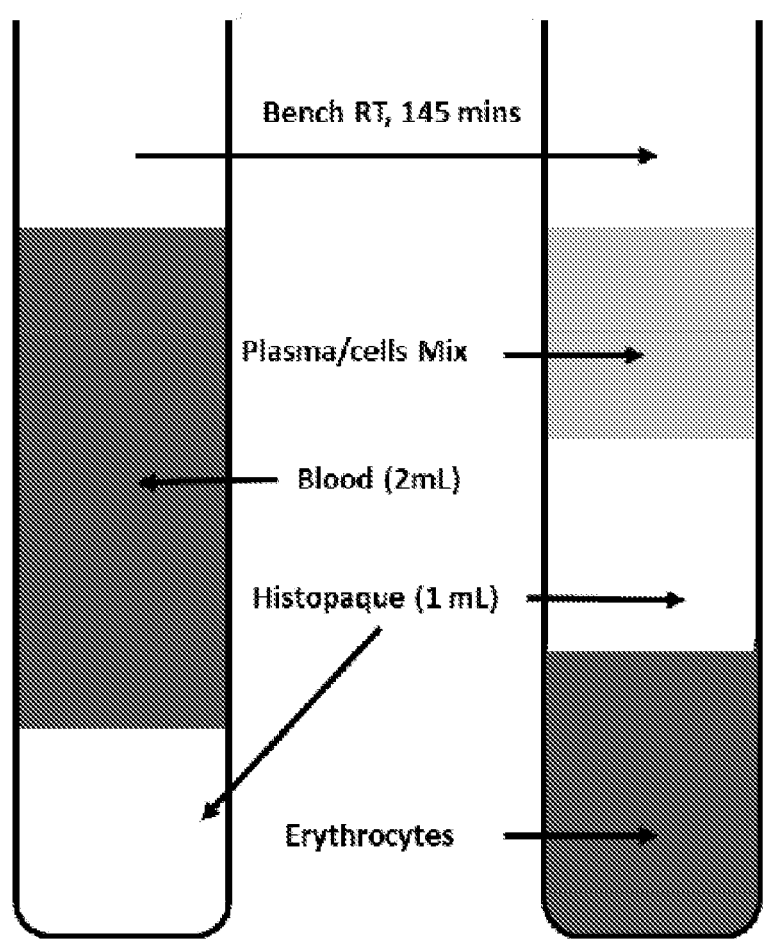
FIG. 2 is a diagram to represent how histopaque may be used to separate blood into (i) plasma with cells and (ii) erythrocytes.

Example 3—CD16b Detection in Buffy Coat and
Cell Preparations Buffy Coat and Histopaque
Investigations For a reproducible buffy coat collection methodology, a histopaque gradient separation column method was used. This involved carefully layering 2 mL of blood over 1 mL of histopaque and leaving it at room temperature for 145 mins. This then gently separates the erythrocytes from the plasma and white blood cells to leave a plasma/cells mix that can be removed without disturbance of the erythrocytes. See FIG. 2.

Using the histopaque method, it was possible to take the plasma/cells mix and separate by centrifugation to give plasma and a pellet of white blood cells. As flow cytometry was being used to count the number of cells present, a sample of the cells was investigated along with the plasma/cell mix from EDTA and lithium heparin blood, with and without lysis.

The lysis of the buffy coat was performed by adding 0.125% Triton x100 to the running buffer (PBS). Another lysis method was also investigated which is the addition of water, which causes lysis of cells by osmosis. The results from this can be found in Table 10.

TABLE 10

Raw data obtained for AF1597 antibody deposited on CN95 with cells and histopaque plasma/cells mix (BC) collected from lithium heparin and EDTA tubes with and without lysis buffer (TX100 and $H_2O$).

| Sample | Neat | +0.125% | +Water |
|---|---|---|---|
| Cell Prep (GNvC) | 7.5 | 12 | 3.5 |
| Histopaque BC EDTA | 81 | 62 | 60 |
| Histopaque BC Lith. Hep. | 58 | 31 | 19 |

As can be seen from Table 10, when the cells prepared for flow cytometry (so not freshly isolated) were tested in the assay there was a much lower signal compared to plasma. When the cells were lysed/solubilised there was little to no specific signal gain with either Triton or water. The cells provided in this preparation were suspended in a buffer that was preferred for flow cytometry; so it was unclear if this buffer was having a detrimental effect on the assay at this stage. When the buffy coat was removed from the histopaque treated blood, and lysed, there was a drop in specific signal from the neat with both lysis methods. This suggested that the cells need to be collected from the histopaque method and resuspended in the current running buffer (PBS) to see if the lysis was having the desired effect.

To isolate the cells from the histopaque buffy coat mix, two aliquots were centrifuged at 400×g for 10 minutes to sufficiently pellet the cells. The supernatant was then removed (retained for testing) while the cells were resuspended in the same volume of PBS, one was kept (and labelled "cells"), the other was centrifuged again to completely wash the cells of any the soluble form of CD16b component (labelled "washed cells"). These were investigated with three lysis methods, TX100 (0.125%), $H_2O$ and a cell extraction buffer provided by ABCAM in their ELISA pack. The results for this testing can be found in Table 11 and FIG. 3.

TABLE 11

Raw data obtained for AF1597 antibody deposited on CN95 with histopaque plasma/cells mix (BC), cells and washed cells collected from EDTA tubes with and without lysis buffer (TX100, $H_2O$ and CEB).

| Sample | Neat | +0.125% TX | +Water | CEB(1%) |
|---|---|---|---|---|
| Histopaque BC | 51 | 54 | | |
| Histopaque BC supernatant | 72 | 77 | | |
| Cells | 14 | 27 | 12 | 3.1 |
| | 12 | 33 | | |
| Washed Cells | 3.7 | 64 | 2.5 | 15 |
| | 3.6 | 33 | | |
| | 5.5 | 56 | | |

Figure 3:
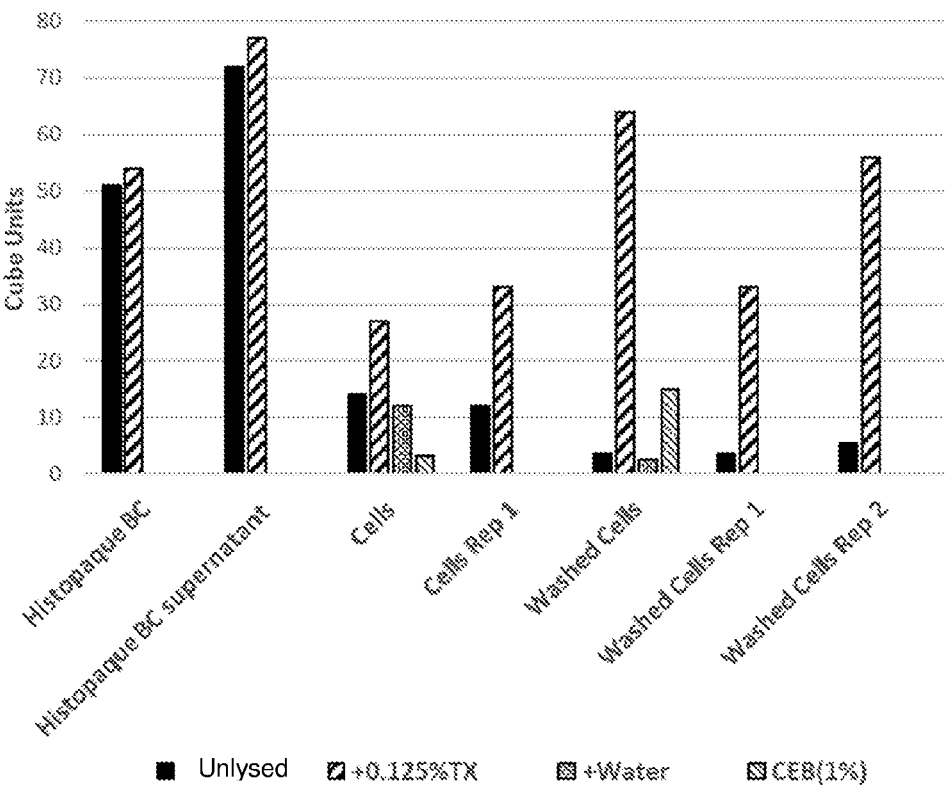
FIG. 3 is a bar graph to represent the change in cube units for AF1597 deposited onto CN95 at 1 mg/mL (PBS+1% sucrose) with AF1597 conjugated to gold with buffy coat (BC), cells and washed cells collected from histopaque processed EDTA blood with and without the addition of Triton x100, water and cell extraction buffer (CEB) as lysis buffers.

As can be seen from FIG. 3, when the buffy coat from the histopaque was measured, there was a small increase in signal obtained with the supernatant from the cell preparation step. This suggested that there was a small release of CD16b from the cells through the process and these values were not affected from the addition of lysis buffer (TX100). When the cells were isolated and measured in PBS, there was a significant drop in signal compared to the plasma. This suggested that the soluble component of the CD16b was in the plasma and had been measured throughout. When the cells were lysed with TX100, there was an increase in specific signal which was not seen when water and CEB were used as lysis buffers. To see if this effect was real, the cells were again lysed with TX100. This showed an increase in signal again suggesting the effect was real. To conclusively know if lysis was indeed solubilising cellular CD16b and the number of cells present, the washed cells were also tested with all three lysis buffers. The washed cells showed a significant increase in signal from neat to those lysed by TX100. There was a small increase in signal for the CEB but it was not as high as the TX100. The water, again, showed no increase in signal, this suggested that water was not suitable for lysis/solubilisation. The washed cells were repeated twice with and without lysis, and this again showed that a significant increase in signal could be obtained. As the methodology had been established to now measure cellular CD16b, it was decided to look at five further blood donors to confirm the result and also get the cells counted by flow cytometry.

Example 4—CD16b Detection in Cell Preparations

To confirm the results of Example 3 that the signal obtained from the lysed cells correlated to the number of cells present, five further blood donors were investigated. The cells were prepared and washed as described above. The cells were prepared at different dilutions to gain a better idea of how the cell number changes affect the assay. The dilutions prepared for the first blood sample were 4×, 2×, neat and ½ cells. Blood donors 1113, 1114, 1117 and 1118 were prepared at 2×, neat and ½ cells. To prepare a stock of 2×cells, 800 μL plasma/cell mix was centrifuged, the cells were resuspended in 400 μL PBS. Once the solutions of the cells were prepared, they were split in two and half went to flow cytometry for neutrophil counting and the other half were read in the assay. The results for the five blood donors with the corresponding neutrophil count can be found in Table 12 and FIGS. 4-6.

TABLE 12

Raw data obtained for AF1597 antibody deposited on CN95 with washed
cells collected from EDTA tubes with and without lysis buffer
(TX100) and corresponding cell count from flow cytometry.

| Blood Donor | Washed Cell | Neat | +0.125% TX | Cell Count (x1000) |
|---|---|---|---|---|
| 1109 | x4 | 1.7 | 45 | — |
| | x2 | 3 | 22 | 1333.5 |
| | x1 | 2.7 | 11 | 788 |
| | x½ | 1.5 | 7.9 | 325 |
| 1113 | x2 | 4.9 | 33 | 6820 |
| | x1 | 4.3 | 16 | 1250 |
| | x½ | 2.6 | 5.2 | 670 |
| 1114 | x2 | 15 | 85 | 6240 |
| | x1 | 9.2 | 66 | 4270 |
| | x½ | 6.6 | 36 | 1710 |
| 1117 | x2 | 9.5 | 66 | 3120 |
| | x1 | 7.5 | 32 | 790 |
| | x½ | 3 | 16 | 360 |
| 1118 | x2 | 9.5 | 53 | 4730 |
| | x1 | 6.3 | 30 | 1180 |
| | x½ | 2.1 | 15 | 455 |

Figure 4:
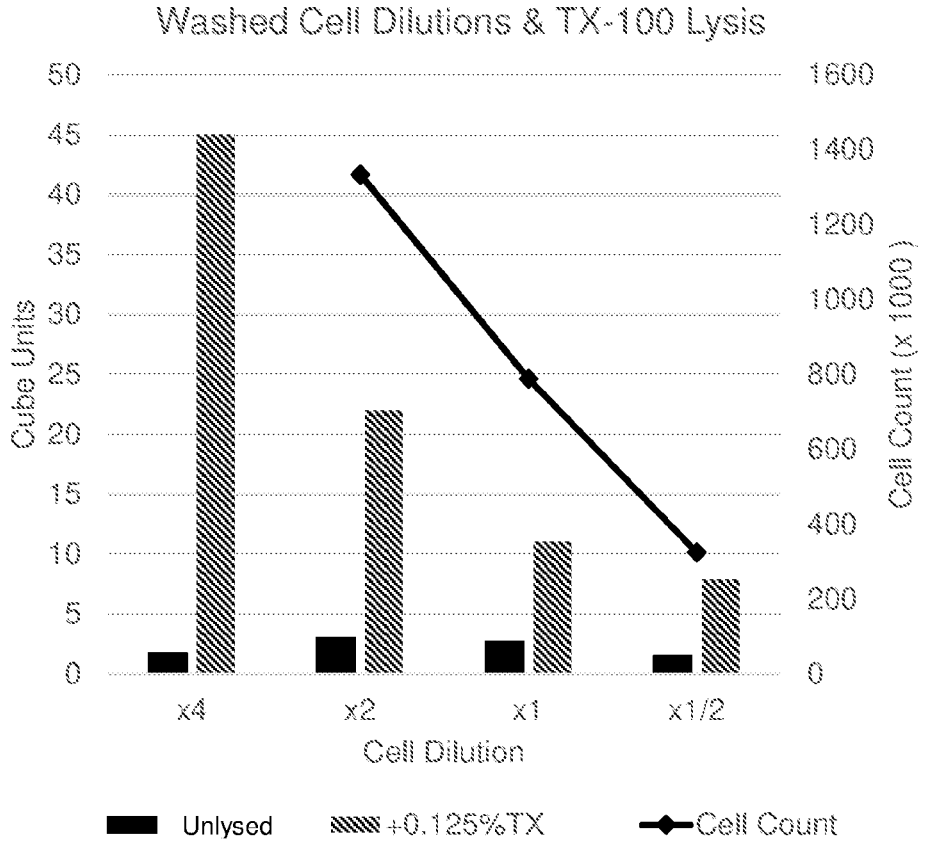
FIG. 4. Is a bar graph to represent the change in test line measurement (cube units) for AF1597 deposited onto CN95 at 1 mg/mL (PBS+1% sucrose) with AF1597 conjugated to gold with washed cells collected from histopaque processed EDTA blood (1109) with and without the addition of Triton x100 and the corresponding cell count by flow cytometry.
Figure 5:
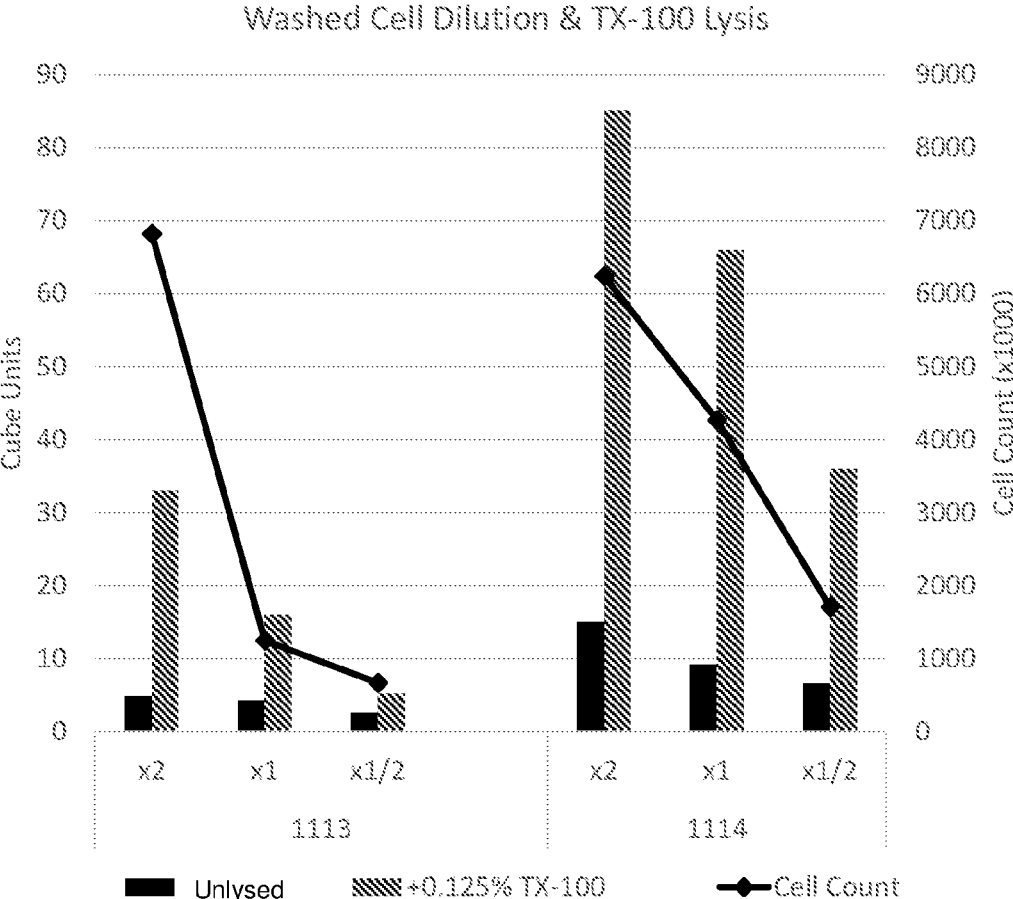
FIG. 5 is a bar graph to represent the change in test line measurement (cube units) for AF1597 deposited onto CN95 at 1 mg/mL (PBS+1% sucrose) with AF1597 conjugated to gold with washed cells collected from histopaque processed EDTA blood donors 1113 and 1114, with and without the addition of Triton x100 and the corresponding cell count by flow cytometry.
Figure 6:
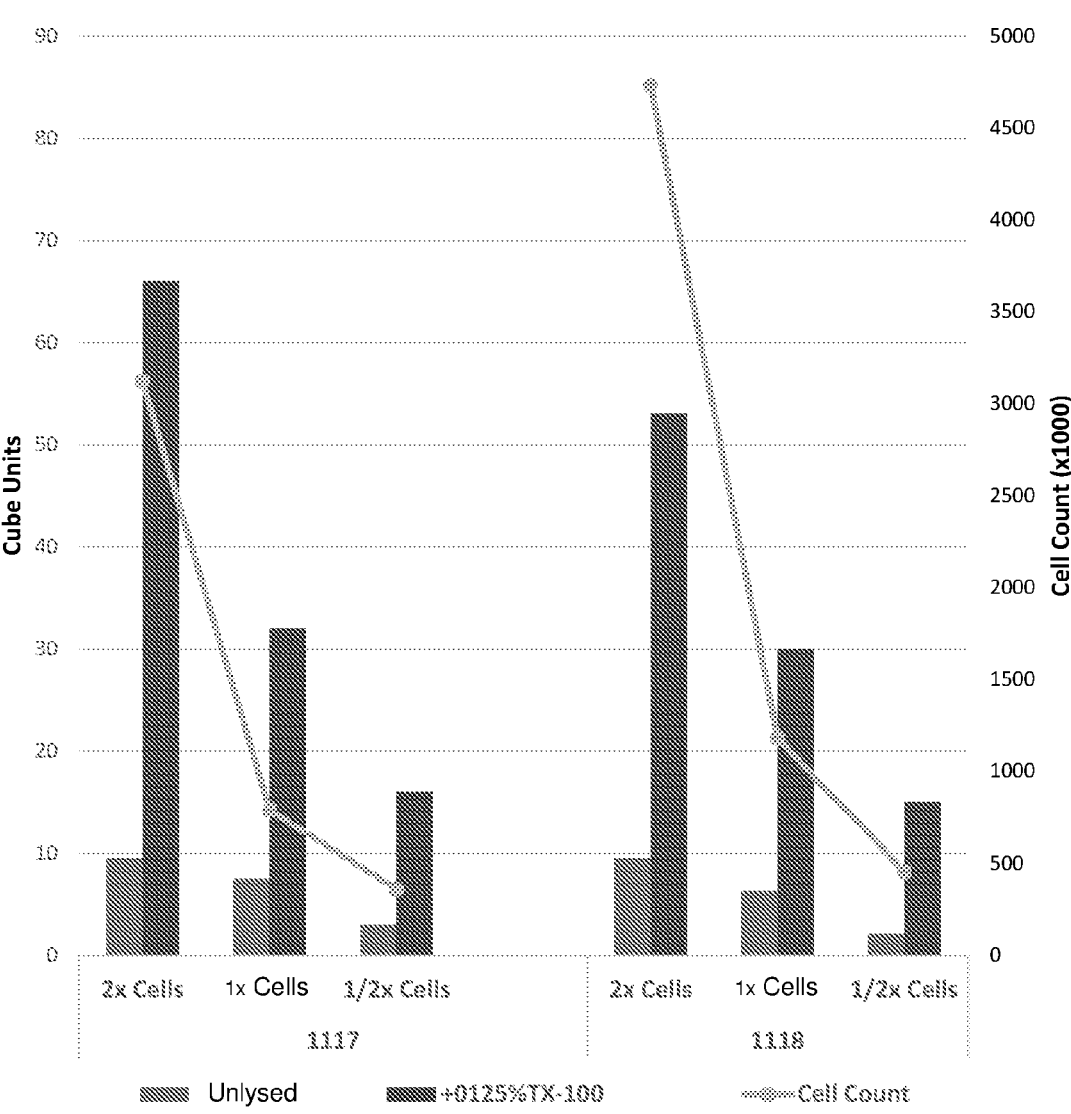
FIG. 6 is a bar graph to represent the change in test line measurement (cube units) for AF1597 deposited onto CN95 at 1 mg/mL (PBS+1% sucrose) with AF1597 conjugated to gold with washed cells collected from histopaque processed EDTA blood donors 1117 and 1118, with and without the addition of Triton x100 and the corresponding cell count by flow cytometry.

As can be seen from FIGS. 4-6, there is a trend for higher number of neutrophils to generate a higher assay signal, and then this count drops along with assay signal suggesting there is a clear relationship between the two. There is one anomalous point in blood sample 1113 where the x2 sample gave a very high cell count but the assay signal is not as high as the 2×sample for 1114. It was discovered in the testing that the white blood cells in the x2 sample had sedimented prior to flow cytometry so this could be the reason the count is higher. The highest assay signal and corresponding neutrophil count is found in FIG. 5 for blood donor 1114. The cell count from flow cytometry shows a high neutrophil count and the assay signal recorded with these was also correspondingly high. This suggests that the higher the neutrophil count the higher the assay signal will be which is to be expected if more cells are available to be lysed. To gain a better understanding of the relationship between the neutrophil count and the assay signal, correlation graphs were plotted. As blood donor 1113 contained an anomalous cell count for the 2×cells, it was removed from the correlation graph. The results for the cube units against the cell count can be found in FIG. 7.

Figure 7:
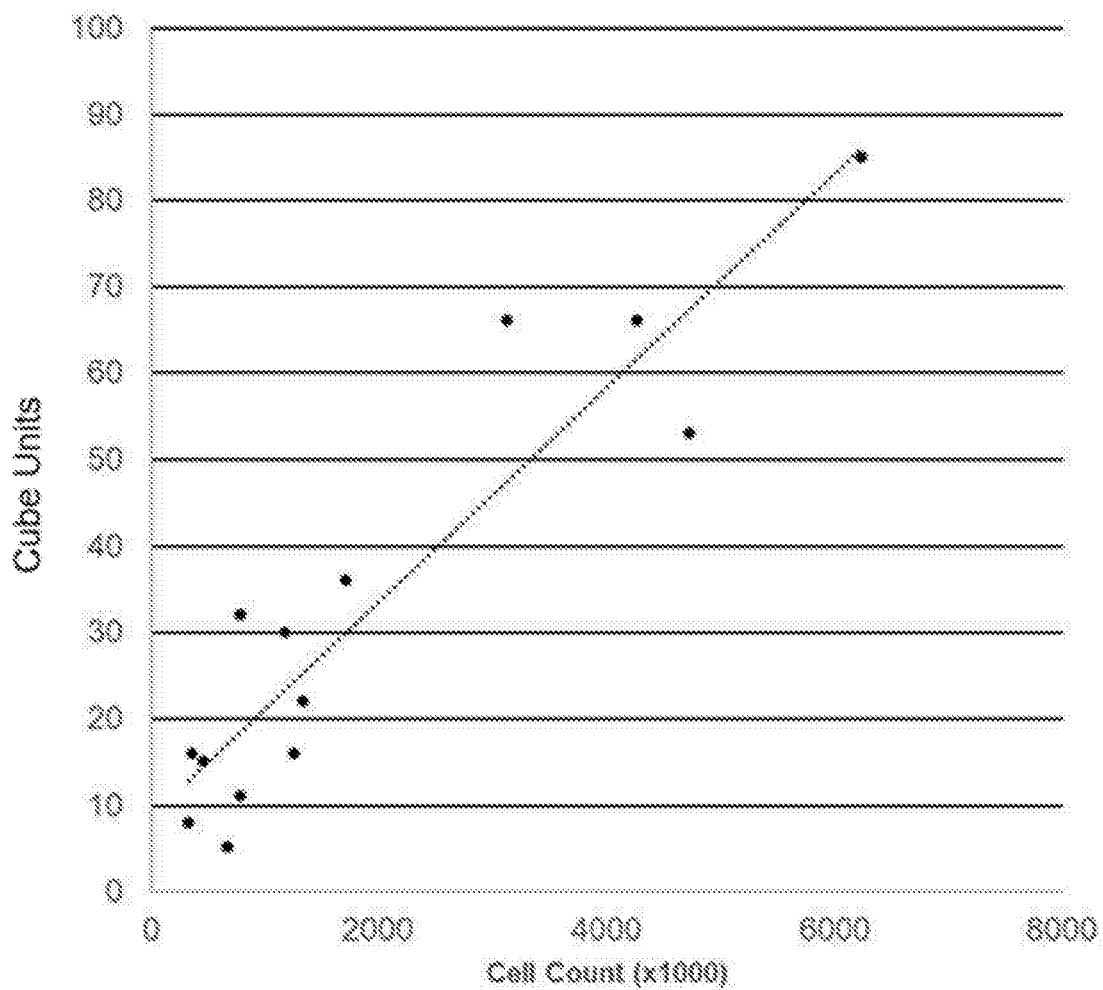
FIG. 7 is a scatter graph to represent the correlation between CD16b measurement (cube units, y-axis) obtained for lysed cells and the corresponding cell count (x-axis) obtained by flow cytometry for five donors, wherein $y=0.0124x+8.8677$ and $R^2=0.861$.
Figure 8:
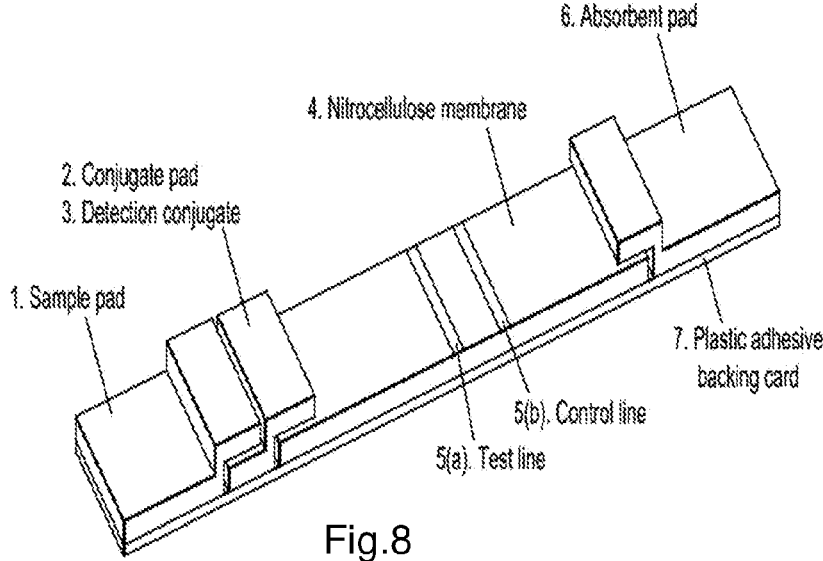
FIG. 8 is a diagram of a typical lateral flow device configuration.

As can be seen from FIG. 7, there is a good correlation between the test line measurement (cube units) obtained for the lysed cells and the neutrophil count obtained by flow cytometry. As can also be seen from FIG. 7, the correlation value (R2) was 0.861. This suggests a good correlation between the cube units obtained and the cell count.

As a correlation had been found between the cellular CD16b (lysed cells) and the neutrophil count, it was decided to see if there was any link between the plasma levels for the different donors and their cellular levels (lysed cells) and cell count. As the plasma/cell mix would contain the same number of cells as a whole blood samples, the comparison was only made with the values obtained for neat cells. The test line measurement (cube unit) results for the plasma against lysed cells and cell count can be found in Table 13.

TABLE 13

Raw data obtained for centrifuged plasma samples from five
blood donors against cube units for lysed washed cells and
the corresponding cell counts obtained from flow cytometry.

| Donor | Plasma | Cell Lysis (Neat) | Cell Count |
|---|---|---|---|
| 1109 | 47 | 11 | 788 |
| 1113 | 184 | 16 | 1250 |

TABLE 13-continued

Raw data obtained for centrifuged plasma samples from five
blood donors against cube units for lysed washed cells and
the corresponding cell counts obtained from flow cytometry.

| Donor | Plasma | Cell Lysis (Neat) | Cell Count |
|---|---|---|---|
| 1114 | 22 | 66 | 4270 |
| 1117 | 163 | 32 | 790 |
| 1118 | 103 | 30 | 1180 |

Example 5—Blood Transport Study

To determine how long a blood sample could be stored, processed and used in the assay, an initial stability experiment was performed. The time points for placing two different blood donors onto the Histopaque were 0, 2, 3.5 and 24 hours. The isolated cells were then measured at 2×, neat and ½ concentration using PBS+0.06% triton as lysis buffer. The results for this blood stability experiment can be found in Table 14.

TABLE 14

Raw data (cube units for CD16b) obtained for different
concentrations of washed cells for two donors at 0,
2, 3.5 and 24 hr time points in wet assay system.

| | | Lysed Washed Cells (+0.06% TX100) | | | |
|---|---|---|---|---|---|
| Blood Donor | Cell Dilution | 0 h | +2 h | +3.5 h | +24 h |
| 1149 | x2 | 25 | 28 | 27 | 17 |
| | x1 | 15 | 18 | 16 | 19 |
| | x½ | 13 | 12 | 11 | 15 |
| 1151 | x2 | 40 | 31 | 31 | 37 |
| | x1 | 36 | 24 | 37 | 23 |
| | x1½ | 38 | 17 | 16 | 25 |

The results show a good reproducibility of results for 0, 2 and 3.5 hour time points. At 24 hours, the results began to plateau suggesting that the blood needed to be processed or sampled prior to this time. From this data it can be determined that the blood can be stored at ambient temperature for 3.5 hours without impact.

Example 6—Further Anti-CD16b Antibody Testing

RP02 Conjugation and Optimisation

Figure 9:
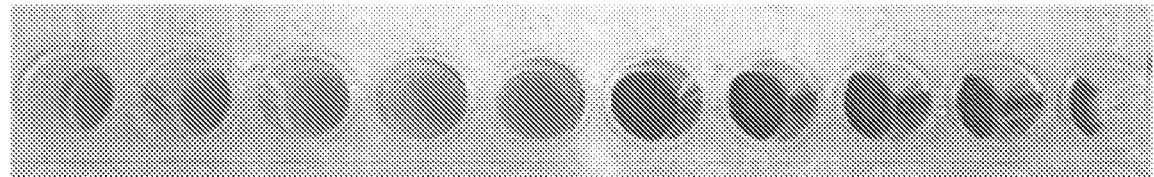
FIG. 9 is a picture to show the aggregation of 40 nm gold with RP02 antibody conjugated at 15 µg/ml in different buffers and different pHs.

A new antibody (RP02) was identified for testing as it was cheaper than the AF1597 antibody. To determine RP02's suitability, a gold optimisation test was performed with the antibody (as was described in Example 1). The results for the aggregation ratio testing (which informs which buffer is most suitable for conjugation) can be found in FIG. 9. As can be seen from FIG. 9, there was only one buffer that met the criteria for suitable conjugation of RP02 antibody and that buffer was borate pH 9.3. After conjugation, the gold is usually resuspended in a gold drying buffer and tested. In this case, there was no drying buffer that was suitable for the antibody as they caused aggregation after being resuspended. This suggested that RP02 could not be used on the gold and as a result it was deposited onto the test line and tested against AF1597 gold.

RP02 Wet System Testing

To test the suitability of the RP02 for use on the nitrocellulose, RP02 was deposited onto CN140 nitrocellulose in 1% sucrose and tested against AF1597 AuC (at 30 µg/mL).

The initial results showed that the use of RP02 on the test line gave an increase in non-specific binding (NSB) whilst giving a good specific signal increase. In an attempt to lower the NSB, the running buffer was changed from PBS to PBST. The system was also tested using two different CD16b antigens (sourced from Sinobio and R&D systems) which were used to produce the two test antibodies, RP02 and AF1597.

A good standard curve was obtained for both types of CD16b. There was a specific signal gain with 10 ng/ml for both types of analyte. The top end of the assay (1000 ng/ml) also gave good comparability for both CD16b antigens, although differences were observed in mid CD16b range (SO-200 ng/mL), with the R&D systems antigen (AF1597 immunogen) having a lower response when compared to the Sinobio systems antigen (RP02 immunogen). As the AF1597 self-pair system showed good response with washed cells, it was decided to see how the RP02/AF1597 system would compare.

RP02 Testing with Washed Cells

To test the RP02/AF1597 test strips using CN95 NC with lysed washed cells, two blood donors were obtained and the white blood cells processed as described in Example 3. The RP02/AF1597 system was then compared to the AF1597 self-pair to ensure good comparability between the two systems. The various processed components of the blood were also measured to include, plasma (from spun blood), plasma (buffy coat after Histopaque treatment) and different concentrations of the washed cells.

The cube units obtained for the washed cells at the different concentrations gave very comparable results for both systems. Differences were observed when measuring the different plasmas for the two donors. The AF self-pair system gave very comparable results for the spun and buffy coat plasmas when both donors were measured. The RP02 system, however, showed differences between the types of plasma, with the spun plasma giving a much lower value when compared to the buffy coat plasma.

Initial RP02/AF1597 Dry Down System

To further the development of the RP02 (CN95 NC)/ AF1597 (AuC) test system, the reagents were dried down. Initially, the volume of the gold conjugate (2.4, 4 and 6 µL) to be dried down was investigated to determine the best specific signal gain. The CD16b standards (Sinobio) were initially spiked into PBST and were also spiked into PBS for comparison.

The results show that when CD16b was spiked into PBST, the specific signal was lower than that obtained when spiked into PBS, for all volumes of deposited gold conjugate. When CD16b was spiked into PBS and tested, a good specific signal increase was observed at 200 ng/ml and then 1 µg/ml at the 4 and 6 µL gold conjugate volumes. In contrast with 2.4 µL gold, the curve plateaued with 1 µg/ml giving no increase in signal above 200 ng/ml. At the top end the 4 µl gold gave the best signal in PBS, the signal being reduced at 6 µl. To explore this further, two additional volumes were assessed to see if a better signal could be found.

The 200 ng/ml standard gave very comparable results for all volume of gold conjugate. The 500 ng/ml standard was found to be highest on the 3 µL deposit which was then lower but comparable for both the 4 and 5 µL deposits. The 1000 ng/ml standard was very comparable for the 3 and 4 µL deposits which then decreased at 5 µL of deposit. The best condition was seen with 4 µL of gold deposit as there was good specific signal difference for all concentrations of CD16b tested, comparable to a high concentration of analyte with wet gold conjugate at the same volume. As the 4 µL showed the best performance it was taken forward for further testing with two different conjugate pads (8951 and 8980). Here the AF1597 AuC conjugate was sprayed onto the two pads using an Isoflow plotter.

The results show a good curve was obtained for both conjugates pads in the dry assay system. The 8980 conjugate pad performed better than the 8951 giving a better specific signal across the standard curve range. This suggested that the best conjugate pad for testing in subsequent sections would be the 8980 conjugate pad.

Example 7—Biotin Testing

Initial Biotin System Testing

Figure 10:
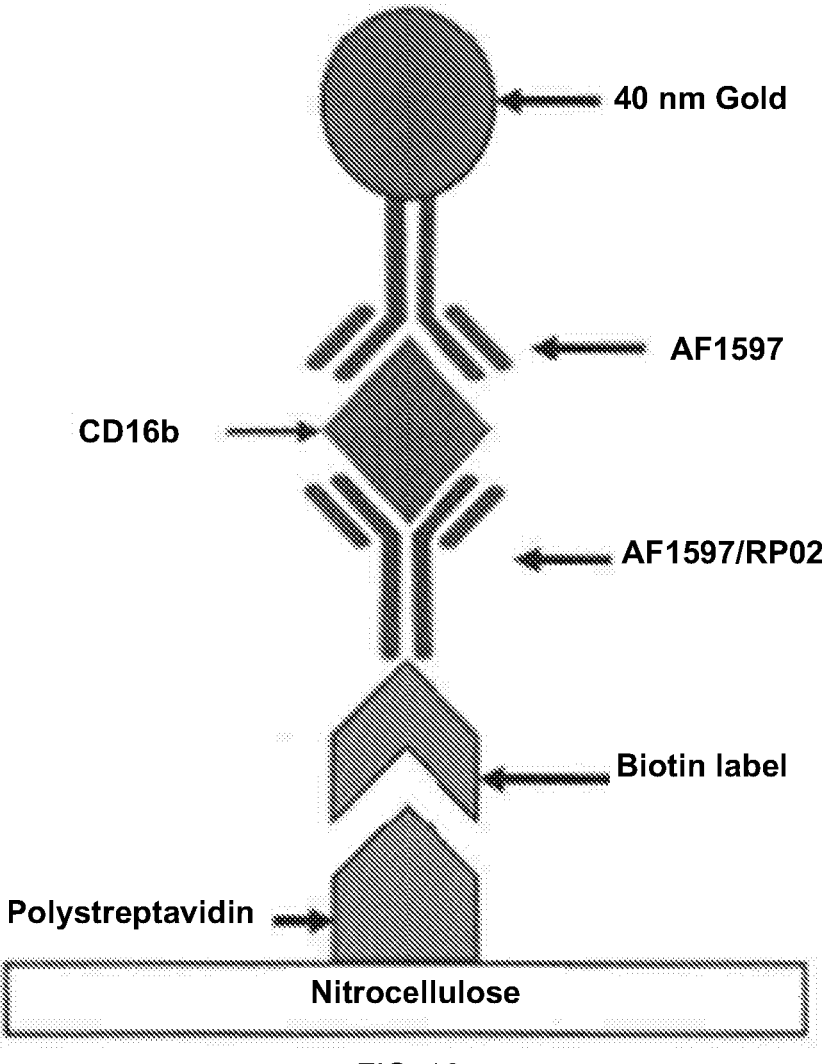
FIG. 10 is a scheme to demonstrate how the biotin system works.

To see if the sensitivity of the system could be enhanced, a polystreptavidin-biotin system was evaluated; this can also help reduce costs as antibodies are typically more expensive. In this system, polystreptavidin was plotted on the test line of CN140 NC and the antibodies RP02 or AF1597 conjugated to biotin and AF1597-gold were combined and dotted onto the conjugate pad. In the presence of the CD16b antigen the biotinylated and gold antibodies form a sandwich with CD16b and the resulting complex will then bind to the polystreptavidin test line. This is shown schematically in FIG. 10. A slower CN140 NC was used in this set up to allow more time for the sandwich to form before reaching the test line.

The antibodies RP02 and AF1597 were biotinylated using a Biotinylation Lightning Link Kit (@ 2 mg/ml) and then diluted 1 in 100 to a final concentration of 16.7 µg/ml. In the initial testing, 4 µL of the biotin conjugate was mixed with 4 µL of the gold conjugate and 20 µL of CD16b analyte in PBS.

The results show that a good specific signal was obtained at 10-200 ng/ml CD16b for both the AF1597 and RP02 biotin systems, with both demonstrating a hook effect at 1000 ng/ml. It can also be seen that the Sinobio CD16b analyte, whilst giving the full assay range, showed lower specific signal for the lower end of the curve. As a hooking effect was observed for high concentrations, it suggested that there was a lack of biotin conjugated material and that a higher volume would be required. To test this, 8 µL of the biotin conjugate was used with the same volume of gold.

The results show that when the volume of biotin conjugate was increased from 4 to 8 µL, a better standard curve was obtained. A difference in specific signal was seen between 200-1000 ng/ml suggesting the hook effect observed using 4 µL of conjugate had been overcome. As a good standard curve had been obtained for the biotin system, a comparison to the previous system where antibody is deposited on the nitrocellulose was performed. Here, 4 µL of ⅟₅₀ diluted biotin conjugates were used to mimic the 8 µL of ⅟₁₀₀ dilutions used in the previous experiments.

The results show that there is very good comparability between both the biotin and the non-biotin system with both giving a good standard curve. That being the case, the biotin system was dried down to assess its performance and suitability compared to the gold conjugate system.

Biotin Dry Down Testing

As a dry system is required for the final device, the biotin system was dried down to assess its performance and suitability as a system to be taken forward. As the dry down requires two components (gold and biotin conjugate), it was decided to investigate if the two conjugates could be dried down mixed together or if they needed to be separated on the pad.

The results show that when the biotin and gold conjugates were mixed together and dried down, high non-specific binding was seen along with only small increases in specific signal and poor standard curve resolution. However, when the two were dried down separately on the conjugate pad lower non-specifics were observed for both systems suggesting the mixing of the materials had led to the increase in non-specific signal. The AF1597 biotin conjugate (with AF1597 AuC) showed a very shallow standard curve with low specific signal increase between 10-200 ng/ml. The RP02 biotin conjugate (with AF1597 AuC) showed a better standard curve response with good signal difference seen between 10-200 ng/ml which was comparable to the initial dry down curve for the RP02 antibody on the test line format. Thus, a good proof of concept was achieved for the biotin system.

Example 8—Whole Blood Testing

Lysis Time Course

As the design of the device requires the lysis of cells isolated from whole blood, it was important to try and determine the time this process would take. It was found that a lysis time of 5 minutes gave a good signal response. This would require a pre incubation of the cells with lysis buffer prior to being run on the lateral flow strip. To determine at which time the cells gave the most consistent signal, a time course was set up sampling at intervals of 0, 1, 3 and 5 minutes. The results for this testing can be found in FIG. 11.

Figure 11:
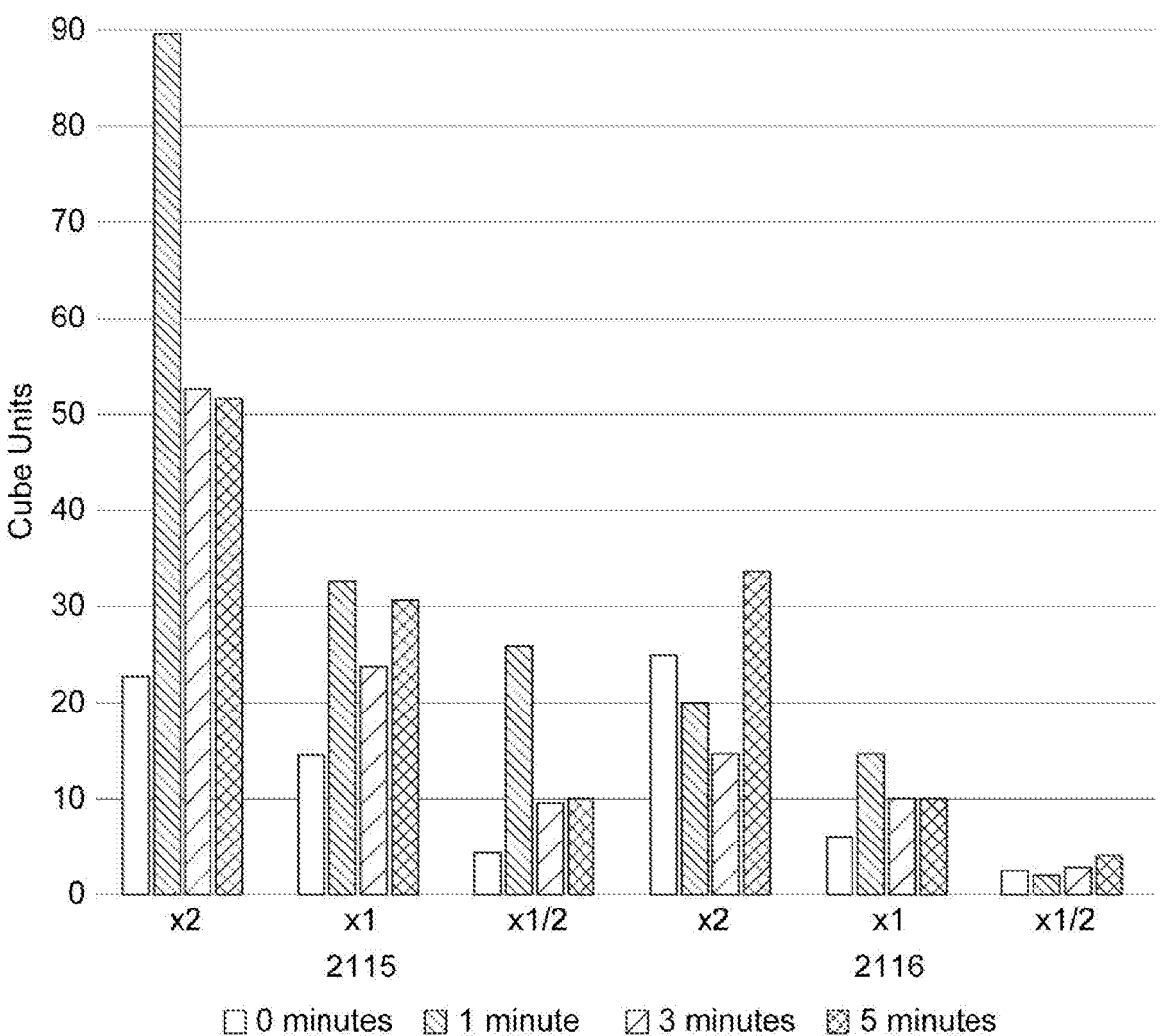
FIG. 11 is a graph to demonstrate the change of cube units for different concentrations of isolated cells from two blood donors with increasing lysis incubation time (0, 1, 3 and 5 minutes shown from left to right for each assay) in wet assay system with RP02 on CN95 NC and AF1597 AuC.

As can be seen from FIG. 11, when the cells are lysed for 5 minutes a good curve is obtained for both blood donors. When the cells are lysed for 3 minutes, a similar curve is obtained for both donors. The biggest difference is noticed for the x2 cells after 3 minutes lysis, where a lower signal was obtained. This could be an anomalous result as this is the lowest signal recorded for all three concentrations for this blood donor. As the results showed that 3 and 5 minutes were the best it was decided to keep 5 minutes as a lysis time for further experiments.

Example 9—Trapping and Lysis of White Blood Cells within the CD16b Lateral Flow Device The trapping and lysis of washed white blood cells was demonstrated within the CD16b lateral flow assay utilising a filter in the form of a sample pad membrane under the sample application window to trap the cells. Washed white blood cells from EDTA blood were used. It was determined that a range of filters may be used to trap neutrophils, for example PES10 (2 orientations), MLRF-NANO-1 (LF1) and MLRF-NANO-2 (LF2) or no cell membrane (filter). It was determined that a range of surfactants may be used for the cell lysis step, for example 0.03% TX-100, 0.03125% SDS or 0.0125% Sarkosyl.

Example 10—Dry Assay Standard Curve

In the dry assay format of the lateral flow test, the test strip was prepared using a CD16b antibody-gold conjugate sprayed and dried onto two different conjugate pads (8951 & 8980; Ahlstrom Munksjo). Dry strips were constructed using conjugate pads at the base, overlapping with a CN95 nitrocellulose membrane (Sartorius) plotted with an anti CD16b antibody (11046-RP02-SIB; Stratech) as a test line, then a sink pad at the top. CD16b standards (Stratech) were spiked into PBS at a range of concentrations from 10-1000 ng/mL. 50 µL of each standard was run up the dry strips followed by 30 µL of PBS and then the test read @ 10 minutes on a cube reader. The results for this testing can be found in Table 15.

TABLE 15

Raw data obtained for varying concentrations of CD16b in PBS with dried sprayed gold conjugate on two conjugate pads (8951 and 8980) with a 10 minute read time.

| Standard | 10 min read | |
| --- | --- | --- |
| CD16b ng/mL | 8951(CP) | 8980(CP) |
| 0 | 5.6 | 9.6 |
| 10 | 9.8 | 25 |
| 50 | 32 | 41 |
| 100 | 55 | 71 |
| 200 | 65 | 83 |
| 500 | 95 | 134 |
| 1000 | 152 | 157 |

Example 11—Lactate Assay

Figure 12:
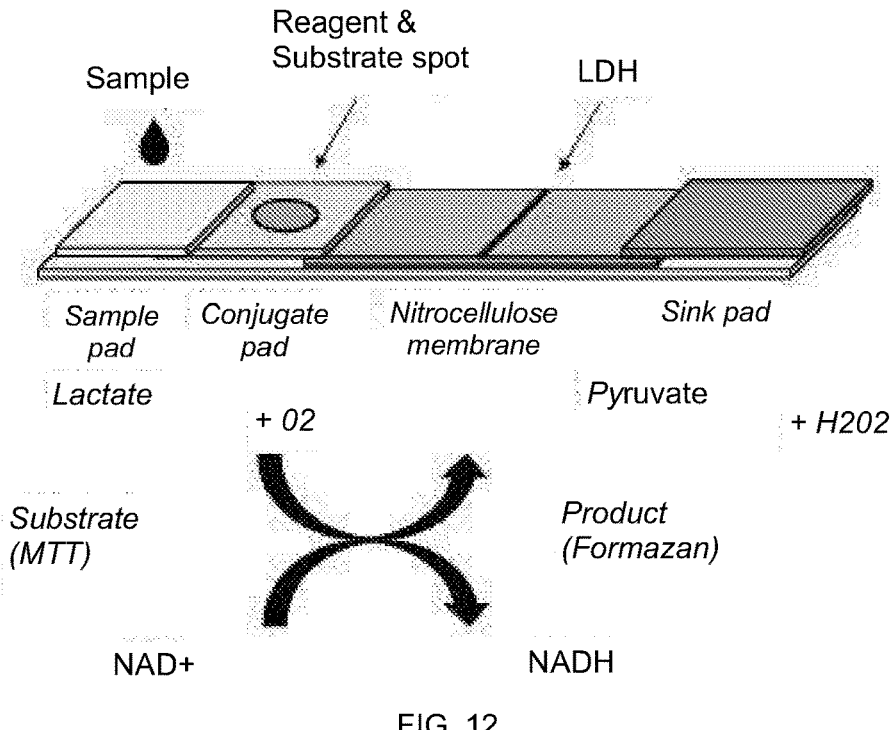
FIG. 12 is a proposed format for the lactate assay and the overall enzymatic reaction which produces the purple Formazan product.

The format of the Lactate assay is based on the enzymatic activity of lactate dehydrogenase. This was achieved by immobilisation of the lactate dehydrogenase enzyme on a nitrocellulose membrane and the inclusion of a dye in the form of a yellow tetrazole (3-(4,5-dimethylthiazol-2-yl)-2, 5-diphenyltetrazolium bromide (MTT)) which can be converted to a purple precipitate called Formazan ((E, Z)-5-(4, 5-dimethylthiazol-2-yl)-1, 3-diphenylformazan) in the presence of lactate through the reduction of NAD+ to NADH during its conversion to pyruvate. (NB: other reagents can be used here to form different formazans). The overall proposed format can be found in FIG. 12.

Lactate Assay Standard Curve

Figure 13:
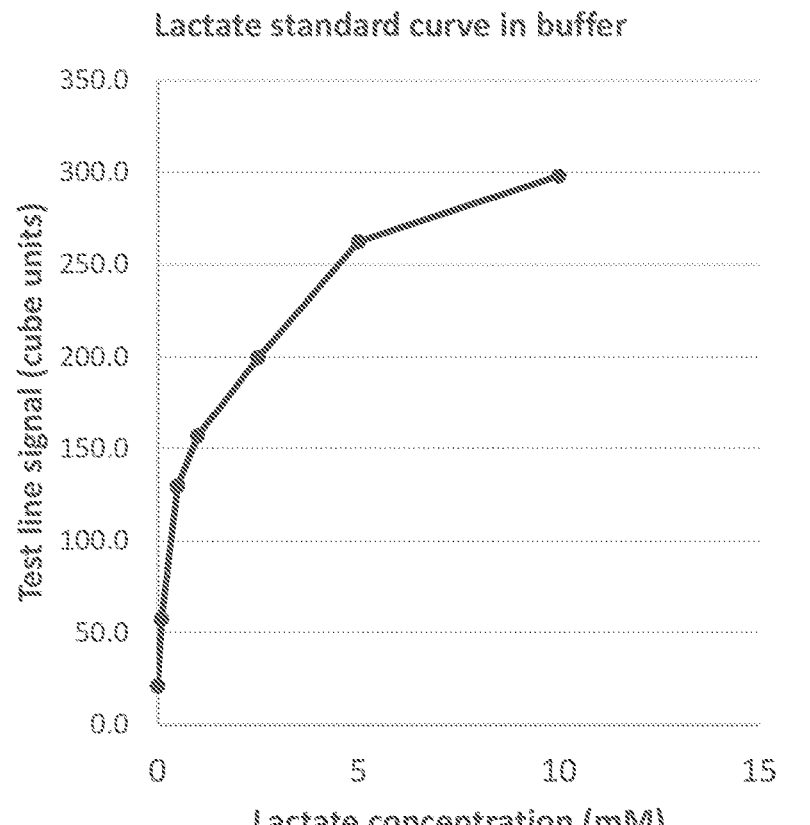
FIG. 13 is a graph to demonstrate the change in cube units for varying concentrations of Sodium Lactate in triplicate with dried dye mix on the conjugate pad (8951) at a 10 minute read time.

A dry lateral flow assay was constructed using a dye mix (containing MTT) deposited and dried onto a conjugate pad (8951; Ahlstrom), overlapping with a CN95 nitrocellulose membrane with an LDH test line plotted at 1 mg/mL. Sodium Lactate was spiked into PBS at a range of concentrations from 0.1-10 mM and 80 µL of each standard was run up the dry strips (in triplicate) and read at 10 minutes on a cube reader. The results for this testing can be found in Table 16 and FIG. 13.

TABLE 16

Raw data obtained for varying concentrations of Sodium Lactate, dye mix dried on conjugate pad & triplicate LDH test line signal measured in Cube units.

| | Test Line Signal (Cube Units) | | | | | |
| --- | --- | --- | --- | --- | --- | --- |
| Lactate (mM) | Rep1 | Rep2 | Rep3 | Mean | Stdev | % CV |
| 0 | 18 | 19 | 26 | 21.0 | 4.36 | 20.8 |
| 0.1 | 55 | 61 | 56 | 57.3 | 3.21 | 5.6 |
| 0.5 | 120 | 125 | 144 | 129.7 | 12.66 | 9.8 |
| 1 | 188 | 134 | 149 | 157.0 | 27.87 | 17.8 |
| 2.5 | 218 | 171 | 210 | 199.7 | 25.15 | 12.6 |
| 5 | 267 | 266 | 254 | 262.3 | 7.23 | 2.8 |
| 10 | 301 | 299 | 294 | 298.0 | 3.61 | 1.2 |

Combined Detection of CD16b and Lactate

The strip design for whole blood requires a blood separator to retain the cells and stop them being lysed prior to running the CD16b portion of the assay. This blood separator will allow the plasma to be run through the strip which will give the lactate assay result. The initial volume of whole blood to be tested was 20 µL with an additional 50 µL of PBS to potentially fully wash all the plasma from the blood (and therefore from the sample pad). It was hoped that the higher volume of blood would give a higher volume of plasma, and thus, would give a better lactate response.

The results show that when 20 µL of blood is used on FRI separator pad, there is little to no haemolysis onto the conjugate pad which suggests that there is little to no lysis of the blood when running the lactate part of the assay. It can also be seen that after 5 minutes there is a clear response for both the 0 mM (very feint) and 10 mM spiked lactate which is stronger and more intense for the higher concentration. After 10 mins, the response for the 10 mM sample had increased in intensity with a darker and wider line seen. The 0 mM, however, showed a small increase in response but was very similar to that at 5 mins. As the volume of whole blood could be lower for the final device (finger prick volume can be low), it was decided to investigate if a lower volume of whole blood with a higher volume of PBS would still give a response whilst flushing the plasma through the strip better. The results for this testing can be found in FIG. 14.

Figure 14:
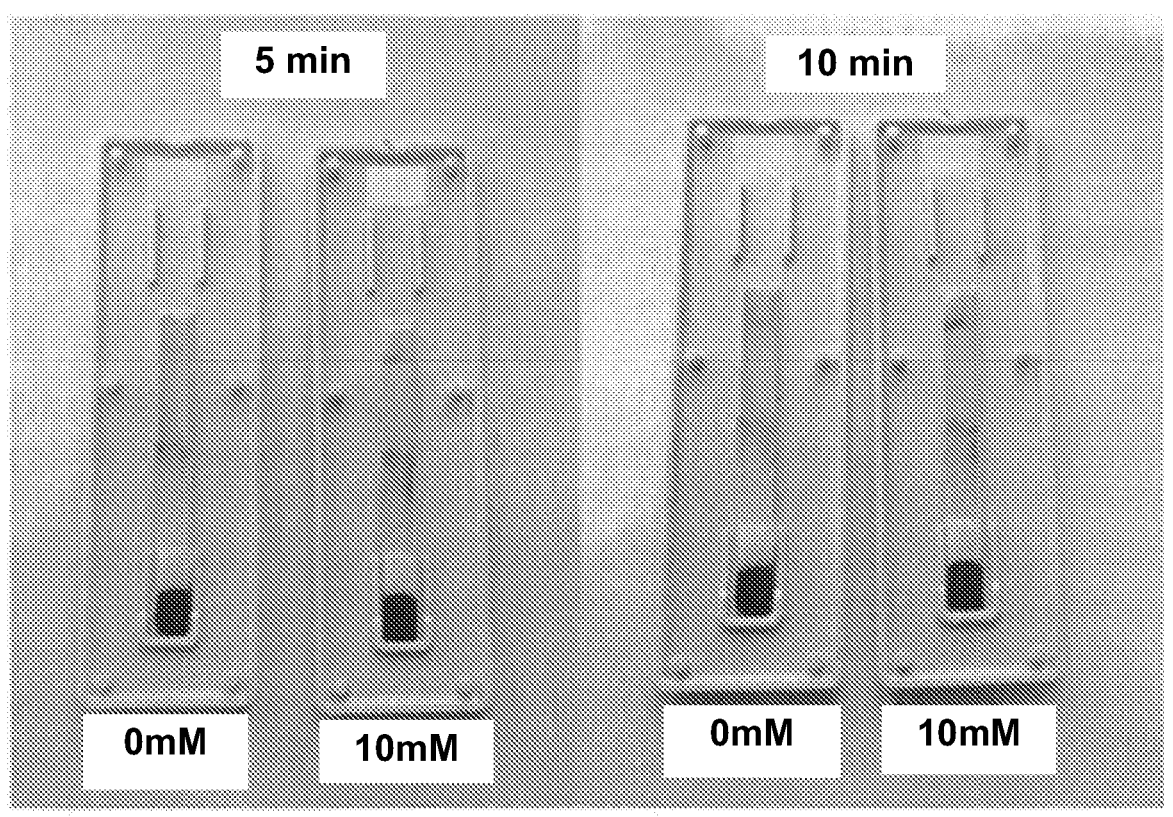
FIG. 14 is a photo to demonstrate the results for 10 µL of whole blood with either 0 or 10 mM spiked Na-L-Lactate chased with 60 µL PBS at either 5 or 10 minutes.

As can be seen from FIG. 14, when 10 µL of whole blood was used with 60 µL of PBS to wash through the plasma there was again little to no haemolysis onto the conjugate pad. This again suggested that even with a lower volume of blood and higher volume of PBS the cells are unaffected. It can also be seen that there is also a clear difference in intensity at 5 minutes between the 0 mM and 10 mM spiked lactate which becomes more apparent at 10 minutes. It can also be seen that there is little to no movement of the formazan product from the test line. These results suggest that it is possible to measure the lactate content of a blood sample whilst also retaining the cells that can then be transferred to the second strip for measurement of CD16b.

Figure 15:
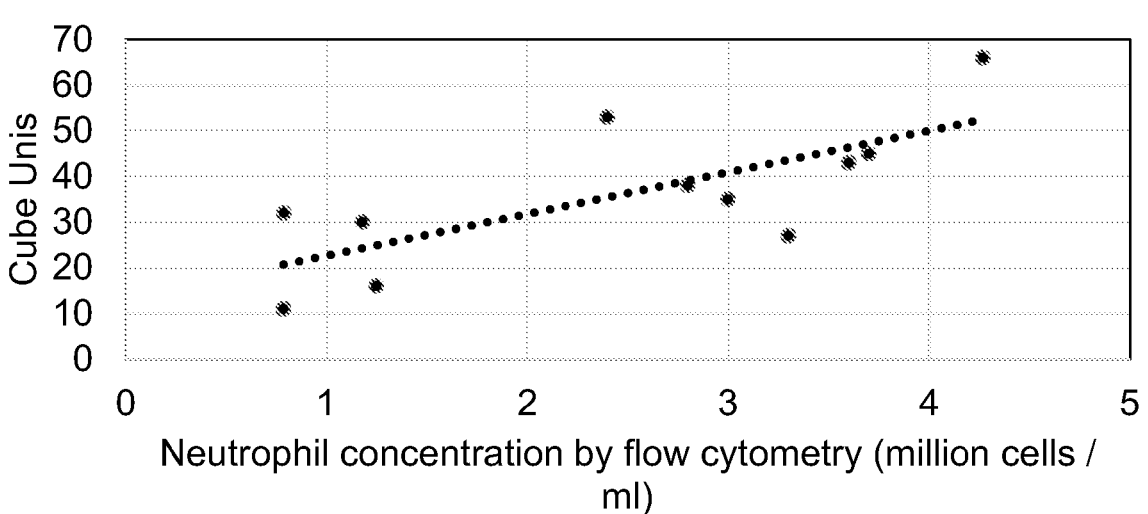
FIG. 15 is a graph to show the correlation between cell-associated (intracellular and membrane-anchored) CD16b and neutrophil levels.
Figure 16:
FIG. 16 is a graph to show the correlation between soluble CD16b and neutrophil levels.
Figure 16:
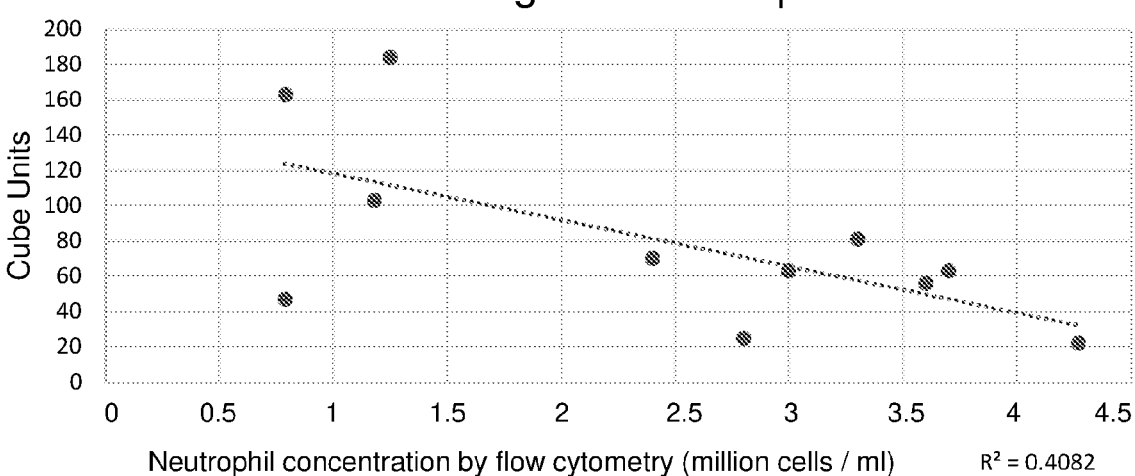
Figure 17:
FIG. 17 is a graph to demonstrate the change in cube units for varying concentrations of CD16b in a wet assay format with a 10 minute read time.
Figure 17:
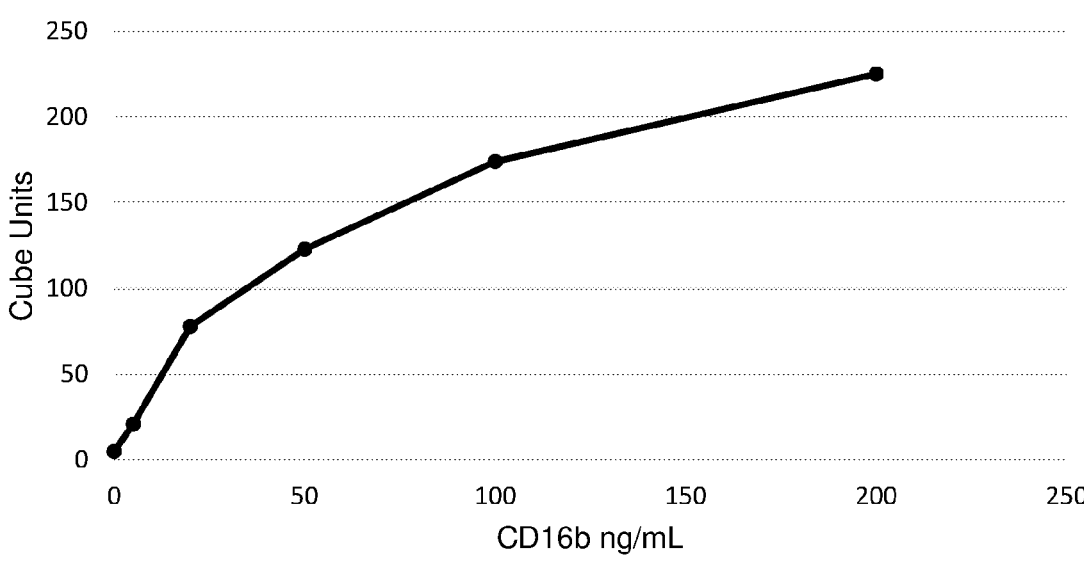

Example 12—Comparative Data for Correlation of the Levels of Soluble CD16b Vs. Membrane-Anchored and Intracellular CD16b with the Number of Neutrophils in a Sample Blood samples were obtained from 11 individuals. Levels of soluble CD16b were examined for correlation with the number of neutrophils. Separately, levels of membrane-anchored and intracellular CD16b (after removal of soluble CD16b and subsequent cell lysis) were examined for correlation with the number of neutrophils. The results show that the cell-associated (intracellular and membrane-anchored) CD16b positively correlates with neutrophil levels (FIG. 15), while soluble CD16b negatively correlates with neutrophil concentration (FIG. 16). The data shows better correlation between the membrane-anchored and intracellular CD16b and neutrophil counts than the soluble CD16b and neutrophil counts (r-squared correlation coefficient of 0.53 (intracellular and membrane-anchored) vs. 0.41 (soluble)). After correction for outliers (3 samples), the R-squared correlation coefficient was 0.8014 for intracellular and membrane-anchored CD16b and 0.3478 for soluble CD16b samples.

The correlation of membrane-anchored and intracellular CD16b with the number of neutrophils is substantially better than the correlation of soluble CD16b with the number of neutrophils. Thus, detection of the levels of membrane-anchored and intracellular CD16b provides a more accurate method for determining the number of neutrophils in the sample.

Example 13—Typical CD16b Standard Curve in a Wet Assay Format

In the wet assay format of the lateral flow test, strips were constructed using a CN95 nitrocellulose membrane (Sartorius) at the base, plotted with an anti CD16b antibody (AF1597) as a test line, then a sink pad at the top. CD16b standards (R&D Systems) were spiked into PBS at a range of concentrations from 5-200 ng/mL. 20 µL of each standard was mixed with 2.4 uL of AF Gold conjugate mixed and run up the wet strips followed by 30 µL of PBS and then the test read @ 10 minutes on a cube reader. The results for this testing can be found in Table 17 and FIG. 1.

TABLE 17

| Raw data obtained for varying concentrations of CD16b in PBS in a wet assay format with a 10 minute read time. | |
| --- | --- |
| CD16b Standard (ng/mL) | Cube Units |
| 0 (PBS) | 5.0 |
| 5 | 21 |
| 20 | 78 |
| 50 | 123 |
| 100 | 174 |
| 200 | 225 |

The invention claimed is:

1. A method of determining a neutrophil level in a sample from a subject, the method comprising:
   determining the level of CD16b in the sample, wherein the CD16b comprises the intracellular form of CD16b, wherein
   (i) the method further comprises a step of removing at least a proportion, most, or all of the soluble form of CD16b from the sample prior to determining the level of CD16b; or
   (ii) the method is performed on a sample from the subject from which at least a proportion, most, or all of the soluble form of CD16b has previously been removed, and
   wherein the step of removing at least a proportion, most, or all of the soluble form of CD16b is a filtration step, wherein the filtration step yields:
      (a) a filtered sample comprising white blood cells, wherein the filtered sample is depleted of the soluble components of the sample; and
      (b) a solution comprising the soluble form of CD16b, and
   wherein determining the level of CD16b in the sample comprises assaying the filtered sample comprising white blood cells for CD16b.

2. The method according to claim 1, wherein the CD16b comprises, consists essentially of, or consists of the membrane-anchored form of CD16b and the intracellular form of CD16b.

3. The method of claim 1, wherein the step of removing at least a proportion of the soluble form of CD16b from the sample is carried out under conditions that keep at least a large proportion, or substantially all of the neutrophils present in the sample intact.

4. The method according to claim 1, wherein the level of CD16b is determined using one or more CD16b-binding antibodies.

5. The method according to claim 1, wherein the sample is from a subject who (i) has been exposed to radiation; (ii) has received or is receiving a drug capable of causing neutropenia; (iii) is suffering from human immunodeficiency virus (HIV), hepatitis and/or an autoimmune disorder; (iv) has cancer and/or has received or is receiving chemotherapy and/or radiotherapy; (v) is displaying or experiencing symptoms of an infection; or (vi) has recently undergone surgery.

6. The method according to claim 1, wherein the method comprises a step of cell lysis prior to determining the level of CD16b in the sample, wherein the step of cell lysis is carried out:

(i) after a step of removing at least a proportion of the soluble CD16b; or (ii) on a sample from which at least a proportion of the soluble CD16b has previously been removed.

7. The method of claim 1, wherein the level of CD16b in the sample is determined via a lateral flow assay.

8. The method according to claim 1, wherein the method further comprises detecting one or more different markers indicative of the presence of sepsis in the sample.

9. The method according to claim 1, wherein at least 2, 3, 4, 5, 6, 7, 8, 9 or 10 or more samples are taken from the subject at different times and the levels of CD16b and optionally one or more further markers are determined and wherein the samples are taken every 6 to 24 hours, daily, or every 2, 3, 4, 5, 6, 7 or 14 days.

10. A method of selecting a subject for treatment with an antibiotic comprising performing the method of claim 1 and selecting the subject for treatment on the basis of the determined neutrophil level.

11. The method according to claim 1, comprising the steps of:

i. adding the sample to a first sample application zone of a first test strip to trap any neutrophils on a filter comprised within the first test strip;

ii. transferring the filter with trapped neutrophils to a second sample application zone of a second test strip;

iii. adding to the filter a lysis reagent to lyse the neutrophils; and iv. determining the level of CD16b.

12. The method of claim 11, wherein the step of determining the level of CD16b comprises:

i. contacting a solution of the lysed neutrophils with a conjugate zone comprising at least one labelled detection moiety which binds to CD16b;

ii. contacting the mixture of the lysed neutrophils and the at least one labelled detection moiety which binds to CD16b with:

(i) a test line for at least CD16b, the test line comprising an immobilised further detection moiety that also binds to CD16b thereby immobilising the CD16b at the test line to produce a signal via the labelled detection moiety also bound to the CD16b; or (ii) a test line for at least CD16b, the test line comprising an immobilised further detection moiety that binds to the CD16b-bound labelled detection moiety of step ii. thereby immobilising it at the test line producing a signal.

13. The method of claim 12 wherein the labelled detection moiety which binds to CD16b is an anti-CD16b antibody conjugated to a gold particle.

14. The method of claim 12, wherein the further detection moiety is an anti-CD16b antibody.

15. The method of claim 11, wherein the lysis reagent is a surfactant, which may be ionic or non-ionic.

16. The method of claim 11, wherein the step of adding the sample to the first application zone is followed by a step of cell wash.

17. The method of claim 11, wherein the filter is a membrane suitable for trapping neutrophils.

* * * * *